US005602015A

United States Patent [19]
Sudhir

[11] Patent Number: 5,602,015
[45] Date of Patent: Feb. 11, 1997

[54] AUTOANTIBODIES WHICH ENHANCE THE RATE OF A CHEMICAL REACTION

[75] Inventor: Paul Sudhir, Omaha, Nebr.

[73] Assignee: Igen, Inc., Gaithersburg, Md.

[21] Appl. No.: 259,151

[22] Filed: Jun. 13, 1994

Related U.S. Application Data

[63] Continuation of Ser. No. 775,956, Oct. 25, 1991, abandoned, which is a continuation-in-part of Ser. No. 343,081, filed as PCT/US90/02274 Apr. 25, 1990, Pat. No. 5,236,836.

[51] Int. Cl.$^6$ .................................................. C12N 9/00
[52] U.S. Cl. ..................... 435/188.5; 435/219; 435/226
[58] Field of Search .............................. 435/188.5, 212, 435/219, 226, 68.1

[56] References Cited

U.S. PATENT DOCUMENTS

| | | | |
|---|---|---|---|
| 4,792,446 | 12/1988 | Kim et al. | 424/85.8 |
| 4900674 | 3/1990 | Benkovic | 435/232 |
| 5,126,258 | 6/1992 | Lerner et al. | 435/188.5 |

FOREIGN PATENT DOCUMENTS

| | | |
|---|---|---|
| 125023 | 11/1984 | European Pat. Off. . |
| WO86/06742 | 11/1986 | WIPO . |
| PCT/US89/01950 | 11/1989 | WIPO . |
| WO90/05746 | 5/1990 | WIPO . |
| WO90/05144 | 5/1990 | WIPO . |
| WO90/07934 | 7/1990 | WIPO . |

OTHER PUBLICATIONS

Shuster, A. M. et al, (1992) Science 256, 665–667.
Paul et al., The Journal of Biological Chemistry, "Site Specificity of a Catalytic Vasoactive Intestinal Peptide Antibody", Jul. 15, 1990, vol. 265, No. 20, pp. 11910–11913.
Kalaga et al., The Journal of Immunology, "Unexpected Presence of Polyreactive Catalytic Antibodies in IgG from Unimmunized Donors and Decreased Levels in Rheumatoid Arthritis", 1995, 155:2695–2702.
Gao et al., The Journal of Biological Chemistry, "Molecular Cloning of a Proteolytic Antibody Light Chain", Dec. 23, 1994, vol. 269, No. 51, pp. 32389–32393.
Paul et al., The Journal of Biological Chemistry, "Cleavage of Vasoactive Intestinal Peptide at Multiple Sites by Autoantibodies", Aug. 25, 1991, vol.266, No. 24, pp. 16128–16134.
Veljkovic et al., Biochemical and Biophysical Research Communications, "Spectral and Sequence Similarity Between Vasoactive Intestinal Peptide and the Second Conserved Region of Human Immunodeficiency Virus Type 1 Envelope Glycoprotein (gp120): Possible Consequences on Prevention and Therapy of Aids", Dec. 15, 1992, vol. 189, No 2, pp. 705–710.
Lee et al., Science, "Functional Interaction and Partial Homology Between Human Immunodeficiency Virus and Neuroleukin", Aug. 28, 1987, 237:1047–1051.

Santis et al., The Journal of Infectious Diseases, "Cross–Reactive Response to Human Immunodeficiency Virus Type 1 (HIV–1) gp120 and HLA Class I Heavy Chains Induced by Receipt of HIV–1–Derived Envelope Vaccines", 1993, 168:1396–403.
Bermas et al., Aids Research and Retroviruses, "Binding of Glycoprotein 102 and Peptides from the HIV–1 Envelope by Autoantibodies in Mice with Experimentally Induced Systemic Lupus Erythematosus and in Patients with the Disease", 1994, vol. 10, No. 9, pp. 1071–1077.
Gololobov et al., Proc. Natl. Acad. Sci. USa, "Cleavage of Supercoiled Plasmid DNA by Autoantibody Fab Fragment: Application of the Flow Linear Dichroism Technique", Jan. 1995, vol. 92, pp. 254–257.
Paul et al., The Journal of Biological Chemistry, "Peptidolytic Monoclonal Antibody Elicited by a Neuropeptide", Jul. 5, 1992, vol. 267, No. 19, pp. 13142–13145.
Kalaga et al., The 9th International Congress of Immunology, "gp 120 Hydrolysis by Catalytic Antibody Light Chain", 1995, abstract #4893, p. 825.
Li et al., The Journal of Immunology, "Catalytic Activity of Anti–Thyroglobulin Antibodies", 1995, 154:3328–3332.
Matsuura et al., Biochemical and Biophysical Research Communications, "Amidase Activity of Human Bence Jones Proteins", Oct. 14, 1994, vol. 204, No. 1, pp. 57–62.
Pauling, L., Nature, 161: 707, (1948).
Kohen, R., Kim, J. B., Lindner, H. R., Eshhar, Z., Green, B., "Antibody enhanced hydrolysis of Steriod esters", (1980) Biochem. Biophys Acta 629, 328–337.
Pollack, S. J., Jacobs, J. W., Schultz, P. G., Science, 234, 1570 (1986).
Tramontano, A., Amman, A. A., Lerner, R. A., J. Am. Chem. Soc., 110, 2282 (1988).
Janda, K. D. Schloeder, D., Benkovic, S. J., Lerner, R. A., "Induction of An Antibody that Catalyzes the Hydrolysis of an Amine Bond", Science, 242, 1188–1191 (1988).
Durfor, C. N., Bolin, R. J., Sugasawara, R. J., Massey, R. J., Jacobs, J. W., Schultz, P. G., J. Am. Chem. Soc. 110, 8713 (1988).
Jackson, D. Y., Jacobs, J. W. Sugasawara, R., Reich, S. H., Bartlett, P. A., Schultz, P. G., J. Am. Chem. Soc., 110, 4841 (1988).
Hilvert, E., Carpenter, S. H., Nared, K. D., Auditor, N. T., Proc. Natl. Acad. Sci. (USA) 85, 4953 (1988).
Shokat, K., Leumann, C. H., Sugasawara, R., Schultz, P. G., Angew. Chem. Int. Ed. Engl., 27, 1172 (1988).

(List continued on next page.)

Primary Examiner—Charles L. Patterson, Jr.
Attorney, Agent, or Firm—Curtis, Morris & Safford

[57] ABSTRACT

Autoantibodies which enhance the rate of a chemical reaction of a substrate, processes for their preparation, their use and compositions thereof are disclosed. In particular, an autoantibody capable of catalyzing the hydrolysis of the peptide bond between amino acid residues $Thr^7$-$Asp^8$, $Arg^{14}$-$Lys^{15}$, $Gln^{16}$-$Met^{17}$, $Met^{17}$-$Ala^{18}$, $Ala^{18}$-$Val^{19}$, $Lys_{20}$-$Lys^{21}$, $Lys^{21}$-$Tyr^{22}$ in the neurotransmitter vasoactive intestinal peptide (VIP) is disclosed.

46 Claims, 20 Drawing Sheets

OTHER PUBLICATIONS

Paul, S., Erian, H. P., Said, S. I., "Autoantibody to vasocative intestinal peptide in human circulation", *Biochem. Biophys. Res. Commun.* 130: 479–485 (1985).

Paul, S., Said, S. I., "Human autoantibody to vasoactive intestinal peptide: Increased incidence in muscular exercise", *Life Sciences* 43: 1079–1084 (1988).

Paul, W., Said, S. I., Thompson, A., Volle, D. J., Agrawal, D. K., Foda, H., De la Rocha, S., "Characterization of antoantibodies to VIP in asthma", *J. Neuroimmunol.*, 23:133–142 (1989).

Itoh, N., Obata, K.-I., Yanaihara, N., Okamoto, H., "Human preprovasocative intestinal polypeptide contains a novel PHI–27–like peptide, PHM–27" *Nature*, 304: 547–549 (1983).

Bloom, S. R., Barnes, A. J., Adrian, T. E., Polak, J. M., "Autoimmunity in diabetics induced by hormonal contaminants of insulin" *Lancet* i: 14–17 (1979).

Paul, S., Said, S. I., "Characterization of receptors for vasoactive intestinal peptide from the lung"*J. Biol. Chem.*, 262: 158–162 (1987).

Turner, J. T., Bylund, D. G., "Characterization of the VIP receptor in rat submandibular gland: Radioligand binding assay in membrane preparations" *J. Pharmacol Exp. Therap.* 242: 873–881 (1987).

Steinitz, M., G., Klein, Koskimies, S., Makela, O., "EB Virus induced B lymphocyte lines producing specific antibodies" *Nature*, 269: 430–422 (1977).

Steinitz, M., Seppala, I., Eichmann, K., Klein, G., "Establishment of a Human Lymphoblastoid Cell Line with Specific antibody production against group A streptococcal carbohydrate" *Immunobiology*, 156:41–47 (1979).

Steinitz, M., Izak, G., Cohen, S., Ehrenfeld, M., Flechner, I., "Continuous production of monoclonal rheumatoid Factor by EBV–transformed lymphocytes", *Nature*, 287: 443–445 (1980).

Kozbor, D., Steinitz, M., Klein, G., Koskimies, S., Maketa, O., "Establishment of anti–TNP antibody–producing human lymphoid lines by preselection for hapten binding followed by EBV transformation:" *Scand. J. Immuol.*, 10: 187–194 (1979).

Kozbor, D., and Roder, J., "The production of monoclonal antibodies from human lymphocytes" *Immunology Today*, 4: 72–79 (1983).

Roder, J., Cole, D., Kozzbor, D., "The EBV–Hybridoma Technique", *Methods in Enzymology*, 121: 140–167 (1986).

Kohler, G., Milstein, C., "Continuous Cultures of Fused Cells Secreting Antibody of Predefined Specificity", *Nature*, 256: 445–497 (1975).

credote, P., et al., *J. of Neuroscience Res.*, 18, 102–107 (1987).

Dimaline, R., et al., *Biochemica et Biophysica Acta.*, 930, 97–100 (1987).

Opstad, K., *Peptidases*, 8, 175–178 (1986).

Unkeless, J. C., et al., *Ann. Rev. Immunol.*, 6, 251–281 (1988).

Hendershot, L. M., et al., *Mol. and Cellular Bio.*, 8 (10), 4250–5256 (1988).

Baldwin, E., and Schultz, P. G., "Generation of a catalytic antibody by site–directed mutagenesis", *Science*, 244:1152 (1989).

Iverson, B. L., and Lerner, R. A., *Science*, 243:1184 (1989).

Paul, S., Wood, K., Said, S. I. Purification of [$^{125}$I ] —Vasoactive intestinal peptide by reverse—phase HPLC. *Peptides* 5:1085–1087 (1984).

Altschuh, D. et al., "Localization of Antigenic Determinants of a Viral Protein by Inhibition of Enzyme–Linked Immunosorbent Assay (ELISA) with Tryptic Peptides", *J. Immunology Methods*, v. 50, p. 99 (1982).

Amit, A. G. et al., "Three–Dimensional Structure of an Antigen–Antibody Complex at 2.8 A Resolution", *Science* 233:747 (1986).

Amzel, L. M. et al., "Three–Dimensional Structure of Immunoglobulins"*Ann. Rev. Biochem.* 48:961 (1979).

Anglister, J. et al., "NMR study of the Complexes Between a Synthetic Peptide Derived from the B Subunit of Cholera Toxin and Three Monoclonal Antibodies Against It", Abstract, *American Chemical Soc.* (1988), 006–2960/88/0427–0717.

Aruffo, A. et al., "Molecular Cloning of a CD38 cDNA by a high–efficiency COS cell expression system", *Proc. Natl. Acad. Sci.*, 84:8573–8577 (1987).

Atassi, M. Z., "Surface–Simulation Synthesis and Its Application in Protein Molecular Recognition", *Protein Engineering — Applications in Science, Medicine and Industry*, pp. 125–153 Edited by Inouye, M. and Sarma, R., Academic Press (1986).

Azuma, T. et al., "Diversity of the Variable–Joining Region Boundary of λ Light Chains has a Pronounced Effect on Immunglobulin Ligand–Binding Activity", *Proc. Natl. Acad. Sci. USA*, v. 81, p. 6139, (Oct. 1984).

Baldwin, E. et al., "Generation of a catalytic antibody by site–directed mutagenesis", *Science* v. 245, pp. 1104–1107(1989).

Barrett, A. J., *Proteinase Inhibitors* (Editors A. J. Barrett and G. Salvesen), pp. 3–22, Elsevier, London, (1986).

Baum, R., "Catalytic Antibody Cuts Peptide Bond", *C & E N*, 5, 30–33 (1982).

Benjamini, E. et al., "Imunochemical Studies on the Tobacco Mosaic Virus Protein, VI. Characterization of Antibody Population Following Immunization with TMV Protein", *Biochemistry* v. 7, No. 4, pp. 1253–1260 (1968).

Benjamini, E. et al., "Immunochemical Studies on the Tobacco Mosaic Virus Protein. VII. The Binding of Octanoylated Peptides of the TMV Protein with Antibodies to the Whole Protein", *Biochemistry*, v. 7, No. 4, pp. 1261–1264 (1968).

Better, M. et al., "*Escherichia Coli* Secretion of an Active Chimeric Antibody Fragment"*Science*, 240: 1041–1043 (1988).

Chalufour, A. et al., "Rare Sequence Motifs are Common Constituents of Hypervariable Antibody Regions"*Ann. Inst. Pasteur/Immunology*, 138:671, Elsevier, Paris (1987).

Chaudhary, V. J. et al., "A recombinant immunotoxin consisting of two antibody variable domains fused to *Pseudomonas* exotoxin", *Nature* 339: 394 1989).

Chothia, C. et al., "Canonical Structures for the Hypervariable Regions of Immunoglobulins", *J. Mol. Biol.* 196: 901 (1987).

Chothia, C. et al., "The Predicted Structure of Immunoglobulin D1.3 and Its Comparison with the Crystal Structure", *Reports*, 755 (Aug. 1986).

Colman, P. M. et al., "Three–Dimensional Structure of a Complex of Antibody with Influenza Virus Neuramindiase"*Nature* 326: 358 (Mar. 1987).

Corey, D. R. et al., "Generation of a Hybrid Sequence-Single-Stranded Deoxyribonuclease", *Reports* 1401 (Dec. 1987).

de la Paz, et al., "Modelling of the Combining Sites of Three Anti-Lysozyme Monoclonal Antibodies and of the Complex Between One of the Antibodies and its Epitope", *EMBO J.* 5:2, 415 (1986).

Dimaline, R. et al., "Purification and Characterization of VIP from Two Species of Dogfish", *Peptides*, 7(Suppl. 1):21–26 (1986).

Dixon, et al., *Enzymes*, Third Edition, London, (1979), index only.

Edelman, G. M. et al., "Reconstitution of Immunologic Activity by Interaction of Polypeptide Chains of Antibodies", *Proc. Natl. Acad. Sci.*, 50:753–761 (1963).

Emr, S. D. et al., "Sequence analysis of mutations that prevent export of λ receptor, an *Escherichia coli* outer membrane protein", *Nature*, 285:82–85 (1980).

Erhan, S. et al., "Do immunoglobulins have proteolytic activity?", *Nature*, v. 251, pp. 353–355 (Sep. 27, 1974).

Fisher, G., "Acyl Group Transfer–Aspartic Proteinases", *Enzyme Mechanisms* (Editors: M. I. Page and A. Williams), Royal Society of Chemistry, London, 230 (1987).

Franek, F. and Nezlin, R. S., *Biokhimiya*, 28 193 (1963).

Franeck, F. and Nezlin, R. S., "Recovery of Antibody Combining Activity By Interaction of Different Peptide Chains Isolated from Purified Horse Antitoxins", *Folia Microbiol.*, 8: 128–130 (1963).

Gavish, M. et al., "Preparation of a Semisynthetic Antibody", Abstract, *Am. Chem. Soc.* (1978), 006-2960/78/0417-1345.

Geysen, H. M. et al., "A Priori Delineation of a Peptide Which Mimics a Discontinuous Antigenic Determinant", *Molecular Immunology*, 23:7 p. 709 (1986).

Giam, C. Z. et al., "In Vivo and In Vitro Autoprocessing of Human Immunodeficiency Virus Protease Expressed in *Escherichia Coli*", *J. Biol. Chem.*, 263: 124617–14620 (1985).

Gish et al., *J. Med. Chem.*, 14:1 159–1162, (1971).

Harper, J. W. et al., "Enzymatically Active Angiogenin/Ribonuclease A Hybrids Formed by Peptide Interchange", Abstracts, *Am. Chem. Soc.* (1988), 006-2960/88/0427-0219.

Hochman, J. et al., "An Activity Antibody Fragment (Fv) Composed of the Variable Portions of Heavy and Light Chains", *Biochemistry* 12:1130 (1973).

Huse, W. D. et al., "Generation of a Large Combinatorial Library of the Immunoglobulin Repertoire in Phage Lambda", *Science*, 246: 1275–1281 (1989).

Inbar, D. et al., "Localization of Antibody–Combining Sites within the Variable Portions of Heavy and Light Chains", *Proc. Natl. Acad. Sci., USA*, 69:2659 (1972).

Inbar, D. et al., "Crystallization with Hapten of the Fab Fragment from a Mouse IgA Myeloma Protein with Antidinitrophenyl Activity", *J. of Biol. Chem.* 246: 6272 (1971).

Jackson, D. Y. et al., "A Mutagenesis Study of a Catalytic Antibody", *Proc. Natl. Acad. Sci. U.S.A.*, v. 88, pp. 58–62 (Jan. 1991).

Jaton, J. C. et al., "Recovery of Antibody Activity upon Reoxidation of Completely Reduced Polyalanyl Heavy Chains and Its Fd Fragment Derived from Anti-2,4-dinitrophenyl Antibody", *Biochemistry*, 7: 4185–4195 (1968).

Jerne, N. K. et al., "Recurrent Idiotopes and Internal Images", *EMBO J.*, v. 1, No. 2, 243–247 (1982).

Kabat, E. A. et al., "Sequences of Proteins of Immunological Interest (5th Edition)", v. 1, 2, 3, U.S. Department of Health and Human Services (1991), Table of Contents only Klein, J. "Immunology: The Science of Self–Nonself Discrimination", pp.168–169 (John Wiley & Sons, New York) (1982).

Knisley, K. A. et al., "Affinity Immunoblotting. High Resolution Isoelectric Focusing Analysis of Antibody Clonotype Distribution", *J. Immunological Methods*, 95, 79–87, Elsevier (1986).

Koerner and Nieman, "High Performance Liquid Chromatographic Determination of Glucosides", *J. Chromatography* 449, 216–228, (1988).

Kohen, F. et al., "An Assay Procedure for Plasma Progesterone Based on Antibody–Enhanced Chemiluminescence", *FEBS Letters*, 104, 201–205 (1979).

Kubiak, T. et al., "Synthetic Peptides $V_H$ (27–68) and $V_H$(16–68) of the Myeloma Immungolobulin M603 Heavy Chain and their Association with the Natural Light Chain to Form an Antigen Binding Site", Abstract, *Am. Chem. Soc.* (1987), 006-2960/87/0426-7849.

Lee, F. et al., "Isolation and Characterization of a mouse interleukin cDNA clone that expresses B-cell stimulatory factor 1 activities and T-cell and mast-cell stimulating activities", *Proc. Natl. Acad. Sci. U.S.A.* 83:2061–2065 (1986).

Lerner, R. A. et al., "At the Crossroads of Chemistry and Immunology: Catalytic Antibodies", *Science*, 252, 659–667 (May 1991).

Lerner, R. A. et al., "Catalytic Antibodies", *Scientific American*, 258(3), 42–50 (1988).

Lerner, R. A. et al., "Antibodies as Enzymes", *Trends Biochem. Science*, 12(11), 427–430 (1987).

Lorberboum–Galski, H. et al., "Cytotoxic Activity of an Interleukin 2–*Pseudomonas* Exotoxin Chimeric Protein Produced in *Escherichia coli*", *Proc. Natl. Acad. Sci. U.S.A.*, 85: 1922–1926 (1988).

Loh, E. Y. et al., "Polymerase Chain Reaction with Single–Sided Specificity: Analysis of T Cell Receptor δ Chain", *Science*, 243:217–220 (1989).

MacDonald, R. J. et al., "Isolation of RNA Using Guanidium Salts", *Meth. Enzymol.*, 152:219–226 (1987).

Machleidt, W. et al., "Mechanism of Inhibition of Papain by Chicken Egg White Cystatin", (Biomedical Division, Elsevier Science Publishers), v. 243, No. 2, p. 234, (Jan. 1989) 00145793/89.

Mariuzza, R. A. et al., "Structure Basis of Antigen–Antibody Recognition", *Ann. Rev. Biophys. Chem.*, 16: 139 (1987).

Meek, T. D. et al., "Inhibition of HIV-1 Protease in Infected T-Lymphocytes by Synthetic Analogues", *Nature*, 343:96 (1990).

Mierendorf, R. C. et al., "Direct Sequencing of Denatured Plasmid DNA", *Meth. Enzymol.*, 152: 556–562 (1987).

Mutter, M., "The Construction of New Proteins and Enzymes—A Prospect for the Future?", *Agnew. Chem. Int. Ed. Engl.* 24, p. 639 (1985).

Nilsson, A., "Structure of the Vasoactive Intestinal Peptide from Chicken Intestine. The Amino Acid Sequence", *FEBS Letters*, 60: 322–326 (1975).

Nishi, N. et al., "Apparent Autolysis of the N-Terminal Tetrapeptide of VIP", *Chem. Pharm. Bull.* 31(3), p. 1067 (1983).

Offord, R. E., "REVIEW Protein Engineering by Chemical Means?", *Protein Engineering*, v. 1, No. 5, p. 151 (1987).

Orlandi, R. et al., "Cloning Immunoglobulin varible domains for expression by the polymerase chain reaction", *Proc. Natl. Acad. Sci. U.S.A.*, 86: 3833–3837 (1989).

Paul, S. et al., "Affinity Chromatography of Catalytic Autoantibody to Vasoactive Intestinal Peptide", *J. Immunology*, v. 145, No. 4, pp. 1196–1199 (Aug. 1990).

Paul S. et al., "Catalytic Hydrolysis of Vasoactive Intestinal Peptide by Human Autoantibody", *Science*, 244:1 158–1162 (1989).

Paul, S., "A New Effector Mechanism for Antibodies: Catalytic Cleavage of Peptide Bonds", *Cold Spring Harbor Symposium on Immunological Research*, v. 54 (1989).

Paul, S. et al., "Autoabzyme Catalyzed Cleavage of Vasoactive Intestinal Peptide", *Progress in Immunology*, v. VIII, pp. 833–836 (editors F. Melchers et al.) Springer Verlag, Berlin (1989).

Paul, S. et al., "Regulatory Aspects of the VIP Receptor in Lung", *Annals of New York Academy of Science*, v. 527, pp. 282–295 (Jun. 1988).

Paul S. et al., "Elevated Levels of Atrial Natriuretic Peptide and Vasoactive Intestinal Peptide in Exercising Man", Abstract, *Clin. Res.*, 35:112A (1987).

Paul, S. et al., "High Affinity Peptide Histidine Isoleucine–Preferring Receptors in Rat Liver", *Life Sciences*, v. 41, pp. 2373–2380 (1987).

Porter, R. R. et al., "Subunits of Immunoglobulins and their relationship to Antibody Specificity", *J. Cell Physiol.*, 67 (Suppl. 1):51–64 (1966).

Rees, A. R. et al., "Investigating Antibody Specificity Using Computer Graphics and Protein Engineering", *Trends in Biochemical Sciences*, 11: 144 (Mar. 1986).

Rich, D. H., "Inhibitors of Aspartic Proteinases", *Proteinase Inhibitors* (Editors A. J. Barrett and G. Salvesen), Elsevier, pp. 179–217 (1986).

Roberts, S. et al., "The Cloning and Expression of an Anti–Peptide Antibody: A System for Rapid Analysis of the Binding Properties of Engineered Antibodies", (IRL Press Limited, Oxford, England) p. 59.

Roholt, O. et al., "Specific Combination of H and L Chains of Rabbit γ–Globulins", *Proc. Natl. Acad. Sci.*, 51:1 73–178 (1964).

Rosselin, G., "The Receptors for the VIP Family Peptides (VIP, Secretin, GRF, PHI, PHM, GIP, Glucagon and Oxyntomodulin). Specificities and Identity.", *Peptides*, 7 (Suppl. 1): 89–10 (1986).

Ruff, M. R. et al., "CD4 Receptor Binding Peptides that Block HIV Infectivity cause Human Monocyte Chemotaxis", *FEBS Letters*, 211: 17–22 (1987).

Sastry, L., et al., "Cloning of the immunological repertoire in *Escherichia coli* for generation of monoclonal catalytic antibodies", *Proc. Natl. Acad. Sci. U.S.A.*, 86: 5728–5732 (1989).

Schultz, P. G., "Catalytic Antibodies", *Acc. Chem. Res.*, 22: 287 (1989).

Schultz, P. G., "The Interplay Between Chemistry and Biology in the Design of Enzymatic Catalysts", *Science*, 240: 426 (1988).

Shenkin, P. S. et al., "Predicting Antibody Hypervariable Loop Conformation. I. Ensembles of Random Conformations for Ringlike Structures", *Biopolymers* 26: 2053 (1987).

Sheriff, S. et al., "Three–Dimensional Structure of an Antibody–Antigen Complex", *Proc. Natl. Acad. Sci. U.S.A.*, 84: 8075 (1987).

Shokat, K. M. et al., "A New Strategy for the Generation of Catalytic Antibodies", *Nature*, v. 338, pp. 269–271 (Mar. 1989).

Skerra, A. et al., "Assembly of a Functional Immunoglobulin $F_V$ Fragment in *Escherichia coli*", *Science*, 240: 1038–1043 (1988).

Smith–Gill, S. J. et al., "Contributions of Immunoglobulin Heavy and Light Chains to Antibody Specifcity for Lysozyme and Two Haptens", *J. Immunology*, 139:4135 (1987).

Stewart, J. M. et al., "Solid Phase Peptide Synthesis", Pierce Chemical Co., Rockford, Illinois (1984) , Index only.

Sun, L. K. et al., *Proc. Natl. Acad. Sci. U.S.A*, 84:214–218 (1987).

Tramontano, A. et al., "Specificity and Mechanism of Esterolytic Antibodies", *J. of Cellular Biochemistry*, Supp. 11C, Abstract N 417, p. 238 (1987).

Tramontano, A. et al., "Antibodies as Enzymic Catalysts", *J. Cellular Biochemistry*, Suppl. 11C, p. 199, Abstract N 022 (1987).

Van Brunt, J., "Antibodies Find a New Role — As Enzymes", *Biotechnology*, 5: 767 (1987).

Van der Eb, A. J. et al., "Assay of Transforming Activity of Tumor Virus DNA", *Meth. Enzymol.*, 65: 826–839 (1980).

Van Regenmortel, R. H. V., *Synthetic Peptides as Antigens*, Laboratory Techniques in Biochemistry and Molecular Biology Series (Editors R. H. Burdon and P. H. van Knippenberg), 19: 1–39 (1988).

Ward, E. S. et al., "Binding activities of a repertoire of single immungolobulin variable domains secreted from *Escherichia coli*", *Nature*, 341: 544–546 (1989).

Winter, G. P., "Antibody Engineering", *Phil Trans. R. Soc. Lond.*, B 324, 537–547 (1989).

Woie, L. et al., "Increase in Plasma VIP in Muscular Exercise", *Gen. Pharmacol.*, 17: 321–326 (1987).

Wong, G. C. et al., "Human GM–CSF: Molecular Cloning of the Complementary DNA and Purification of the Natural and Recombinant Proteins", *Science*, 228: 810–815 (1985).

Yang, Y. C. et al., "Human IL–3 (Multi–CSF): Identification by Expression Cloning of a Novel Hematopoietic Growth Factor Related to Murine IL–3", *Cell*, 47: 3 –10 (1986).

Yokota, T. et al., "Isolation and characterization of a human interleukin cDNA clone, homologous to mouse B–cell stimulatory factor 1, that expresses B–cell and T–cell stimulatory activities", *Proc. Natl. Acad. Sci. U.S.A.*, 83: 5894–5896 (1986).

*Affinity Chromatography Principles and Methods*, Pharmacia, pp. 12–18, Uppsala Sweden (1986).

*FPLC™ Ion Exchange and Chromatofocusing—Principles and Methods*, Pharmacia, pp. 59–106, Uppsala, Sweden (1987).

PhastGel Silver Kit Instruction Manual, Pharmacia, Uppsala, Sweden (1987).

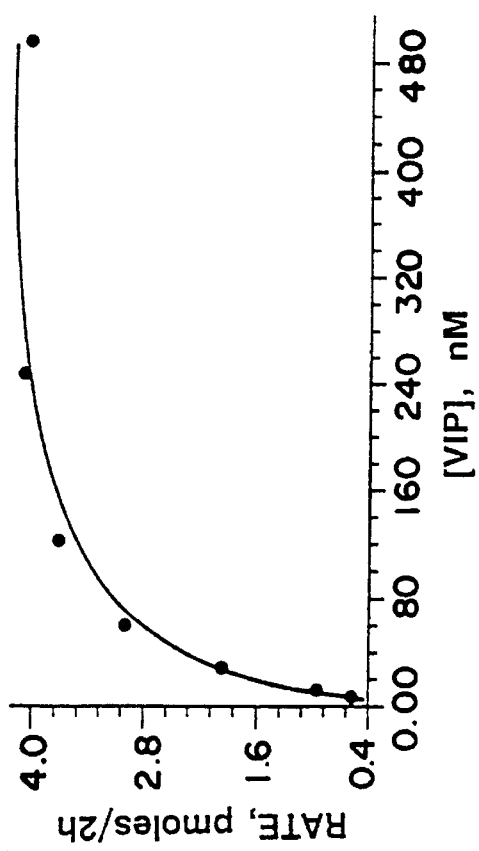
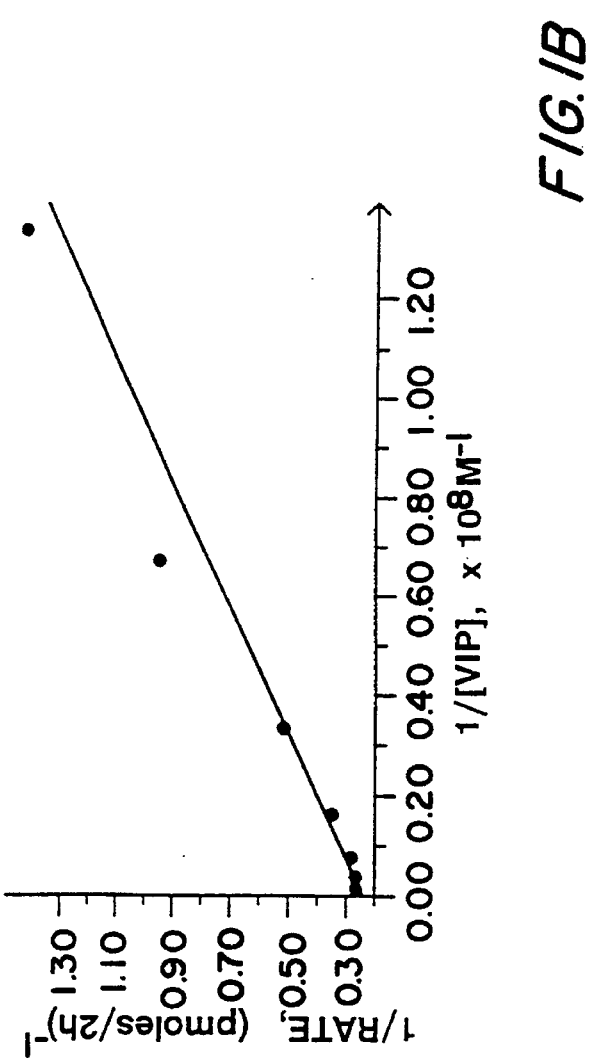
FIG.1A
FIG.1B

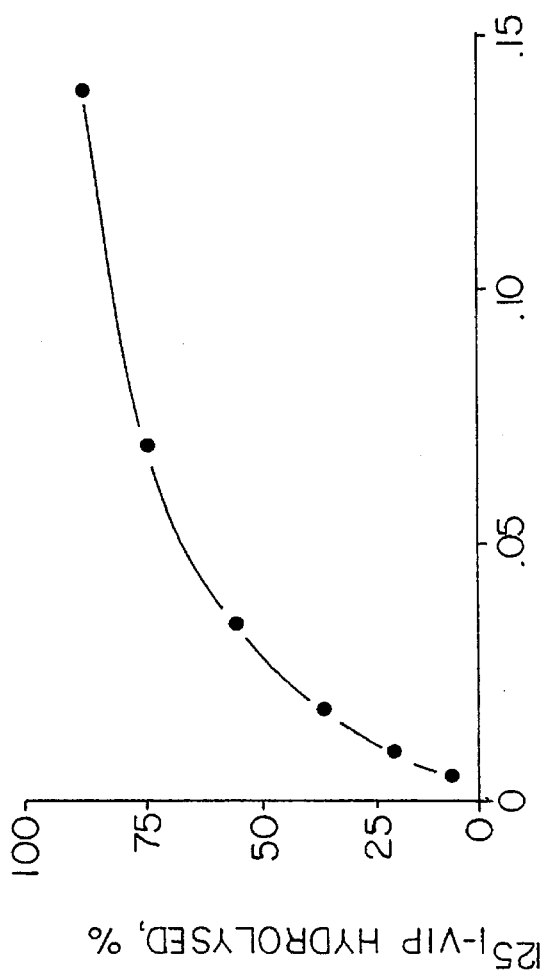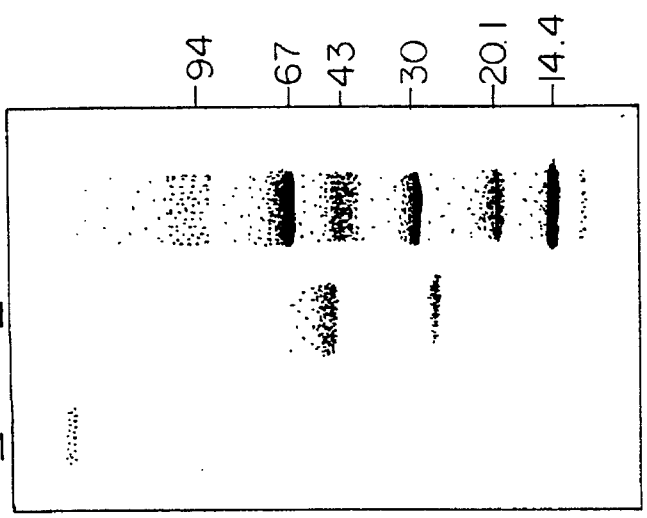

AUTOANTIBODIES WHICH ENHANCE THE RATE OF A CHEMICAL REACTION

This application is a continuation of application Ser. No. 07/775,956, filed Oct. 25, 1991, now abandoned, which is a continuation-in-part of U.S. application Ser. No. 7/343,081, filed as PCT/US90/02274 Apr. 25, 1990, now U.S. Pat. No. 5,236,836, the contents of which are hereby incorporated herein by reference.

FIELD OF THE INVENTION

This invention pertains generally to antibodies and more particularly to naturally occurring antibodies capable of enhancing the rate of a chemical reaction.

Several publications are referenced in this application by Arabic numerals within parentheses in order to more fully describe the state of the art to which this invention pertains as well as to more fully describe the invention itself. Full citations for these references are found at the end of the specification immediately preceding the claims. These publications are incorporated herein by reference.

BACKGROUND OF THE INVENTION

The nature of the forces involved in ligand binding by antibodies and substrate binding by enzymes is similar, viz., hydrogen bonding, electrostatic interaction and hydrophobic effect. The energy obtained from enzyme-substrate binding may be visualized to force electronic strain in the substrate and facilitate the formation of a transition state. There is strong evidence for the theory that enzymes bind the transition state of the reaction they catalyze better than the ground state, resulting in a reduced free energy of activation for the reaction (1). This has come to be known as the transition state theory of enzymatic catalysis. Other factors that may facilitate enzymatic catalysis are the proximity and orientation effects—apposition of correctly oriented reactants within the active site of the enzyme would reduce the requirement for a large number of random collisions prior to a productive reactant interaction. In principle, antibodies could catalyze chemical reactions by similar means.

The first report of chemical conversion of a ligand by an antibody appeared in 1980 (2), but the steroid ester hydrolysis by a rabbit polyclonal antiserum described in this report was stoichiometric rather than catalytic. Subsequently, antibodies have been demonstrated to catalyze or facilitate chemical reactions, including acyl transfer (3), pericyclic (4) and redox reactions (5).

It is generally believed that these antibodies obtain their catalytic properties, like enzymes, from their ability to bind the transition state of the ligand better than its ground state. Antibodies with enzymatic activity offer the possibility of specific, high efficiency catalytic chemical conversion of ligands. Many biological mediators are peptides or proteins, including the antigens of pathogenic organisms, hormones, neurotransmitters and tumor specific antigens. It should be possible to utilize the vast repertoire of specificities that the immune system encompasses to catalyze chemical reactions not within the scope of naturally occurring enzymes. The combination of antibody specificity with the catalytic power of enzymes has the potential of generating potent therapeutic agents, e.g., catalytic antibodies capable of specifically hydrolyzing key vital coat proteins, tumor specific proteins, or endogenous proteins involved in disease. Hitherto, antibody mediated cleavage of peptide bonds has not been demonstrated and, thus, the search for antibodies capable of cleaving specific peptide bonds is of considerable interest. Compared to the type of antibody-mediated chemical transformations achieved thus far, the cleavage of peptide bonds is more energy-demanding.

It was also not known that naturally occurring antibodies, i.e., antibodies produced by an animal's immune system to the animal's own cellular component (self-antigen), as opposed to an antigen introduced by immunization, could enhance the rate of a chemical reaction, e.g., the cleavage of a peptide bond. These so-called autoantibodies, which may be found in autoimmune disease are important in a number of therapeutic strategies.

OBJECTS OF THE INVENTION

It is therefore a general object of the invention to provide autoantibodies which enhance the rate of a chemical reaction.

It is a further object of the invention to provide autoantibodies which catalytically enhance the rate of a chemical reaction.

It is another object of the invention to provide antibodies which enhance the rate of cleavage of a peptide bond.

It is yet another object of the invention to provide a method for preparing autoantibodies which enhance the rate of a chemical reaction.

It is another object of the invention to provide autoantibodies which can be used as therapeutic agents in the treatment of cancer and microbial infection.

It is still another object of the invention to provide methods to diagnose and to treat autoimmune diseases associated with autoantibodies.

These and other objects, features and advantages of the invention will become readily apparent from the ensuing description, and the novel features will be particularly pointed out in the appended claims.

SUMMARY OF THE INVENTION

The invention is broadly directed to an extract of blood serum comprising an autoantibody which enhances the rate of a chemical reaction of a substrate. The autoantibody is prepared by identifying an animal with autoantibodies to a self-antigen of the animal, isolating the autoantibodies and screening the autoantibodies to identify an autoantibody which enhances the rate of the chemical reaction. The rate enhancement can be catalytic or stoichiometric. In an embodiment, the chemical reaction is the cleavage of a peptide bond in the substrate.

The invention is also directed to an extract of blood serum comprising an autoantibody which enhances the rate of hydrolysis of one or more peptide bonds in the neuropeptide vasoactive intestinal peptide (VIP).

In still another aspect, the invention is directed to a method for preparing an autoantibody which enhances the rate of a chemical reaction of a substrate by identifying an animal with autoantibodies to a self-antigen of the animal, isolating the autoantibodies and screening the auto-antibodies to identify an autoantibody which enhances the rate of the chemical reaction. The autoantibodies are polyclonal antibodies. Monoclonal antibodies are prepared by isolating lymphocytes from the so-identified animals, producing a plurality of hybridomas from the lymphocytes and screening the monoclonal antibodies produced by the hybridomas to identify monoclonal antibodies which enhance the rate of the chemical reaction.

In still another aspect, the invention is directed to a composition comprising an extract as described above and an inert carrier, said extract being present in an amount effective to enhance the rate of a chemical reaction of a substrate.

In yet another aspect, the invention is directed to a method for enhancing the rate of a chemical reaction of a substrate which comprises contacting the substrate with an autoantibody which enhances the rate of the chemical reaction and which is prepared by the process described above under conditions sufficient for the chemical reaction to take place.

In another aspect, the invention is directed to a method for enhancing the rate of hydrolysis of peptide bonds formed by amino acid residues 7 and 8, 14 and 15, 16 and 17, 17 and 18, 18 and 19, 20 and 21, and 21 and 22 of vasoactive intestinal peptide which comprises the steps of identifying animals with autoantibodies to vasoactive intestinal peptide, isolating the autoantibodies, screening the autoantibodies to identify an autoantibody which enhances the rate of hydrolysis and contacting an autoantibody so identified with vasoactive intestinal peptide under conditions sufficient for the hydrolysis to take place.

In another aspect, the invention is directed to an autoantibody which enhances the rate of a chemical reaction of a substrate, which autoantibody is prepared by identifying an animal with autoantibodies to a self-antigen of the animal, isolating the autoantibodies and screening the autoantibodies to identify an autoantibody which enhances the rate of the chemical reaction. In one embodiment, the chemical reaction is cleavage of a peptide bond.

In another aspect, the invention is a method for preparing an autoantibody which enhances the rate of a chemical reaction of a substrate. The method comprises identifying an animal with autoantibodies to a self-antigen of the animal, isolating the autoantibodies and ultrafiltering said autoantibodies to identify an autoantibody which enhances the rate of the chemical reaction.

In yet another aspect, the invention is directed to a method for enhancing the rate of cleavage of a peptide bond in a substrate which comprises contacting the substrate with an autoantibody under conditions sufficient for the cleavage to take place, the autoantibody having been prepared by the process defined above.

In another aspect, the invention is a method for treating a disease condition in an animal caused by an autoantibody which enhances the rate of a chemical reaction of a self-antigen of the animal. The method comprises preparing an inhibitor which is capable of binding to the autoantibody and administering to the animal an amount of the inhibitor effective to decrease the rate of said chemical reaction.

In still another aspect, the invention is directed to a method for diagnosing an autoimmune disease in an animal which is caused by an autoantibody enhanced chemical conversion of a self-antigen of the animal. The method comprises contacting the self-antigen with an extract of blood from the animal and screening the autoantibodies to identify an autoantibody which enhances the rate of the chemical conversion.

In another aspect, the invention is a method for treating a disease condition in an animal caused by a substrate which comprises administering to the animal an autoantibody capable of enhancing the rate of cleavage of a peptide or other bond in the substrate in an amount effective to enhance the rate of cleavage of the target bond.

BRIEF DESCRIPTION OF THE DRAWINGS

The invention will be understood more clearly and fully from the following detailed description, when read with reference to the accompanying figures, in which:

FIG. 1 shows mono ($^{125}$I, Tyr$^{10}$)-VIP hydrolysis by IgG: saturation by increasing concentrations of VIP. The data were fitted to be Michaelis-Menton equation using ENZFITTER (Elsevier);

FIG. 7 and 8 show the amino acid sequences of the VIP fragments determined by the Edman degradation method;

FIG. 10 shows Coomassie blue stained hydrolytic IgG (lane 1), the Fab portion of the IgG (lane 2) and molecular weight markers (lane 3) electrophoresed on an 8–25% gradient polyacrylamide gel (A) and a plot of % of $^{125}$I-VIP hydrolyzed versus increasing concentrations of Fab (values are means of 3 replicates the standard deviations values were 0.6% to 3.1%) expressed as the percent of radioactivity rendered TCA soluble by the Fab);

DETAILED DESCRIPTION OF THE INVENTION

Figure 2B:
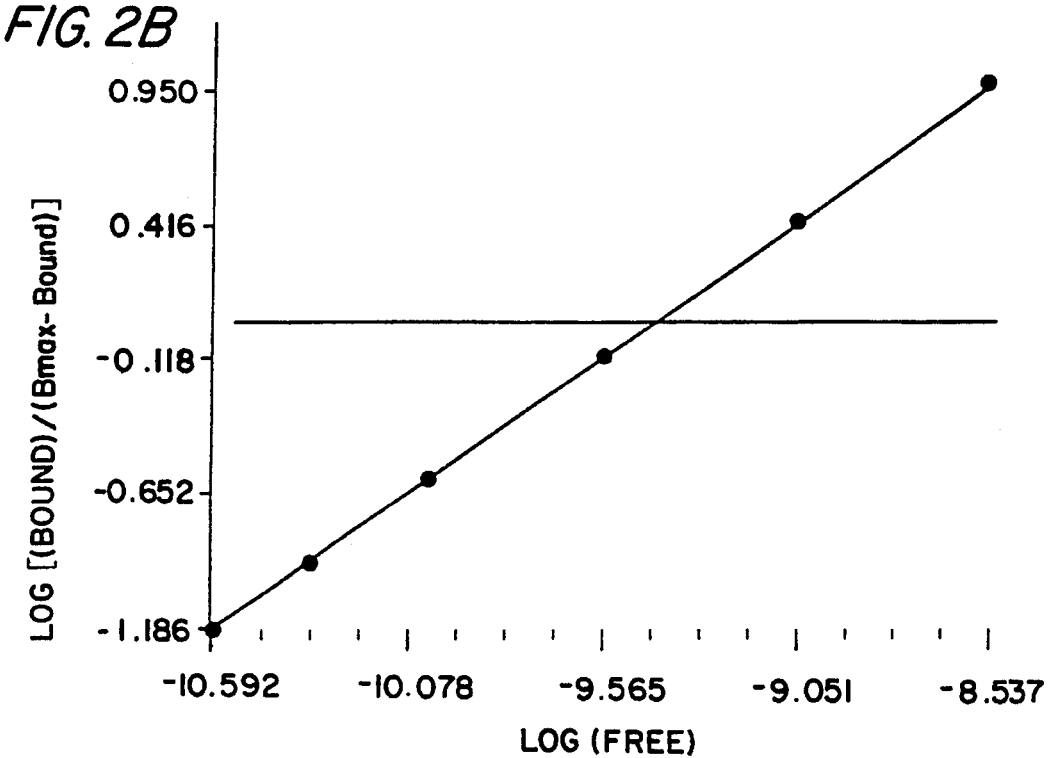
FIG. 2 shows a Scatchard plot (A) and Hill plot (B) of VIP binding by the IgG.

The invention is broadly directed to an extract of blood serum comprising an autoantibody which enhances the rate of a chemical reaction of a substrate. The autoantibody is prepared by identifying an animal with autoantibodies to a self-antigen of the animal, isolating the autoantibodies and screening the autoantibodies to identify an autoantibody which enhances the rate of the chemical reaction. The extract can be blood plasma, purified immunoglobulins (IgG, IgM, IgA, IgD or IgE) or antibody fragments, such as, Fab, F(ab')$_2$, Fv, etc., of immunoglobulins. Chemical reaction refers to a reaction wherein at least one reactant is converted to at least one product. Such chemical reactions include chemical reactions which can be catalyzed by enzymes such as, for example, oxoreductases, transferases, hydrolases, lyases, isomerases and ligases as well as chemical reactions for which no catalytic enzymes are known, such as, for example, oxidations, reductions, additions, condensations, eliminations, substitutions, cleavages and rearrangements.

The term "animal" as used herein refers to any organism with an immune system and includes mammalian and non-mammalian animals. The term "substrate" is synonymous with the reactant in the chemical reaction and can be any of a number of molecules and biomolecules including but not limited to proteins, phospholipids, carbohydrates (e.g., glycogen, glucose, etc.), drugs (including abused substances and drugs from exogenous sources).

Autoantibodies in accordance with the invention are naturally occurring antibodies produced by the immune system of an animal which bind to the animal's own cellular components and which are not elicited by specific immunization against a target antigen. Autoantibodies recognize a self-antigen, i.e., any antigen which the body makes using its own genetic code. Thus, self-antigens are distinguished from foreign antigens (e.g., bacterial, viral antigens). The term "substrate" as defined herein can be the same as or different from the self-antigen.

In one embodiment, the chemical reaction is the cleavage of a peptide bond. Peptide bond as used herein refers to an amide bond linking two adjacent amino acid residues and is generically represented by the following formula wherein the peptide bond is shown within the box:

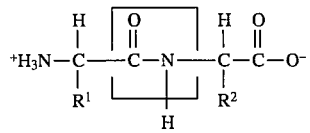

An amino acid consists of a carbon atom to which is bonded an amino group, a carboxyl group, a hydrogen atom and a distinctive group referred to as a "side chain" ($R_1$ and $R_2$ in the formula above). Amino acid as used herein includes the twenty naturally occurring amino acids which comprise the building blocks of proteins. It is understood by those skilled in the art that when either of the adjacent amino acids is proline, the respective side chains $R_1$ or $R_2$ are bonded to the adjacent nitrogen atoms to form the characteristic 5-membered proline ring.

The substrate containing the peptide bond or bonds to be cleaved can be any proteinaceous molecule such as, for example, a regulatory protein or a structural protein, and includes, but is not limited to, peptide hormones (e.g., insulin, growth hormone, secretin, etc.), peptide neurotransmitters and neuromodulators (e.g., vasoactive intestinal peptide, endorphins, enkephlins, bradykinins, substance P etc.) tumor proteins (e.g., oncogene products, carcinoembryonic antigens, etc.), bacterial proteins and viral proteins (e.g., human immunodeficiency viral(HIV) gp 120, influenza glycoproteins, etc.).

An animal with autoantibodies to a target self-antigen of the animal is identified by measuring, in plasma samples or purified IgG from the animal, the saturable binding of the autoantibodies to the self-antigen of the animal itself, to a self-antigen of a different animal species which is identical or substantially identical to the self-antigen of the animal or to a synthetic self-antigen which is identical or substantially identical to the self-antigen of the animal, using methods well known in the art. Autoantibodies which bind to the self-antigen are isolated by standard methods.

Catalytic activity can be induced in the purified autoantibodies by separating from the gamma globulin fraction, derived from serum of an animal identified as having the autoantibodies, molecule(s) which bind to the gamma globulin fraction. Separation of these molecule(s) can be achieved by ultrafiltration, dialysis, washing after immobilization on a non-specific protein support or affinity chromatography on a specific protein support.

The term "ultrafiltration" as used herein refers to a filtering process employing a membrane having pores with an average cut off molecular weight ranging from 1,000 to 10,000 Daltons. Thus, for example, ultrafiltering an immunoglobulin with a molecular weight of 150,000 Daltons on a membrane with pores having an average cut off molecular weight of 10,000 Daltons will cause molecules with molecular weights smaller than 10,000 Daltons to pass through the membrane while the immunoglobulin will remain on the membrane.

The term "dialysis" as used herein refers to a process for separating globular proteins in solution from low-molecular weight solutes which utilizes a semipermeable membrane to retain protein molecules and allow small solute molecules and water to pass through. Dialysis membranes with molecular weight cut-offs ranging from 12,000–15,000 Daltons are advantageously used.

The isolated autoantibodies are then screened for rate enhancement activity. Screening can be conveniently accomplished by treating a standardized solution of the reactant/substrate with an aliquot of medium containing the autoantibodies and measuring the presence of the desired product by conventional instrumental methods. This measurement can be readily conducted, for example, by spectrophotometric methods or by gas-liquid or high pressure liquid chromatography. By comparison with standardized samples of the desired product or reactant/substrate, rates of reaction can be quantified.

The rate enhancement achieved by the antibodies according to the invention is either catalytic or stoichiometric. Thus, antibodies in accordance with the invention which catalytically enhance the rate of the reaction are "catalytic antibodies" and antibodies which stoichiometrically enhance the rate of the chemical reaction are "stoichiometric antibodies".

A catalytic antibody in accordance with the invention is a substance which is capable of changing the rate of a chemical reaction, all other conditions (e.g., temperature, reactant/ substrate concentration, etc.) being the same and which does not enter into the chemical reaction and therefore is not consumed in the reaction. It is also a substance which exhibits the capability of converting multiple moles of reactant/substrate per mole of catalytic antibody; which, from a mechanistic viewpoint, binds the reactant/substrate, effects the accelerated conversion of the reactant/substrate to the product and then releases the product; and which changes the rate of the chemical reaction without shifting the position of the equilibrium. The aforementioned definitions are characteristics of ideal catalysts. However, in practice, even the best of catalysts become poisoned or deactivated by contamination in the reaction system or as a result of chemical or physical destruction during the reaction process. For reasons well known in the art, the true operation of a catalyst may be obscured by components of the reaction system or by the condition of the reaction environment.

A stoichiometric antibody in accordance with the invention enhances the rate of the chemical reaction stoichiometrically. In other words, it enhances the rate of the reaction but, unlike a catalytic antibody, is stoichiometrically consumed during the reaction. Thus, the term "stoichiometric enhancement" implies that the antibody causing the observed rate enhancement enters into the reaction as a reactant and is consumed in the process.

The art has adopted certain working definitions to express catalytic activity. These expressions are [1]$k_{cat}$, or "turnover" and [2] $k_{cat}/k_{uncat}$, the "rate enhancement factor". Turnover indicates the number of molecules of reactant/ substrate which can be converted to product per mole of catalytic antibody per unit time. For example, if a molecule exhibits a turnover of $10^3$ molecules of substrate per minute and the molecule maintains its catalytic activity for 24 hours at room temperature and at its optimal pH, each molecule of catalyst would then make a total of $1.4 \times 10^6$ conversions, indicating its catalytic behavior. This total conversion is to be distinguished from the total conversion in a stoichiometric reaction, which will never exceed 1.0, no matter how long the reaction is carried out. The rate enhancement factor is a dimensionless number which expresses the rate of reaction in the presence of catalyst to the rate of reaction in the absence of catalyst, all other reaction conditions (e.g., reactant concentration, temperature, etc.) being equal.

The invention is also directed to a method for preparing an autoantibody which enhances the rate of a chemical reaction of a substrate. The method comprises identifying an animal with autoantibodies to a self-antigen of the animal, isolating the autoantibodies and screening the autoantibodies to identify one or more antibodies which enhance the rate of the chemical reaction. In an embodiment of the invention, autoantibodies are isolated by separating the gamma globulin fraction from serum collected from the animal and separating from the gamma globulin fraction molecule(s) which bind to the gamma globulin fraction. As noted earlier, these molecules can be separated by ultrafiltration, dialysis, washing after immobilization on a non-specific protein support or affinity chromatography on a specific protein support. Screening in order to detect antibodies with the desired rate enhancement activity can be achieved by, for example, high performance liquid chromatography (HPLC), immunoassays (e.g., radioimmunoassay and nonisotopic immunoassays) or electrophoresis.

The antibodies in accordance with the invention can be monoclonal or polyclonal. If monoclonal antibodies are desired, they can be prepared by isolating lymphocytes from animals identified as having autoantibodies to a particular self-antigen, producing a plurality of hybridomas from the isolated lymphocytes and then screening the monoclonal antibodies produced by the hybridomas to identify monoclonal antibodies which enhance the rate of the chemical reaction. The antibody-producing lymphocytes are hybridized with myeloma cells, such as, for example SP2/0 or NS1 cells, to produce hybridoma cells. These hybridoma cells are then plated in the wells of microtiter plates. The series of monoclonal antibodies being produced by the hybridoma cells is screened under appropriate conditions to identify monoclonal antibodies which enhance the rate of the reaction under appropriate conditions. The identification can be made by treating a standardized solution of the reactant/ substrate with an aliquot withdrawn from a microtiter well and screening for the presence of the desired product, as described above. By comparison with standardized samples of the desired product or reactant/substrate, rates of reaction can be quantified. In this manner, wells containing hybridoma cells producing rate enhancing monoclonal antibodies are identified. The selected hybridoma cells are then cultured to yield colonies.

These colonies can be further propagated in in vitro or in vivo systems. In the latter case, mice such as syngeneic BALB/C mice are inoculated intraperitoneally with the selected hybridoma cells and produce tumors, generally within two or three weeks. These tumors are accompanied by the production of ascites fluid which contains the desired monoclonal antibodies. The monoclonal antibodies are then separately recovered from the ascites fluid by conventional methods such as ultrafiltration, ultracentrifugation, dialysis and immunoaffinity chromatography.

Peripheral blood lymphocytes of an animal identified as having rate enhancing autoantibodies for a particular substrate can be stimulated to grow in culture and, therefore, can be immortalized using methodologies well known in the art. For example, the lymphocytes can be so stimulated using a virus, a chemical agent or a nucleic acid (e.g., an oncogene). A particularly advantageous virus for immortalization is Epstein Barr virus (EBV). Thus, rate enhancing autoantibodies can be produced by the transformed cells. The so transformed cells can then be cloned using known methods to provide a reliable source of large amounts of monoclonal antibodies having rate enhancing activity for a given substrate.

One skilled in the art will appreciate that the genes, or fragments thereof, coding for the variable region of the autoantibody can be expressed in prokaryotic and eucaryotic cells using recombinant DNA methodologies well known in the art. Thus, the prokaryotic and eucaryotic cells are used to propagate the variable region of the autoantibody.

In accordance with an embodiment of the invention, the separately recovered antibodies are contacted with a molecule (e.g., a substrate, self-antigen, etc.) under suitable conditions permitting the formation of a complex between the antibody and the molecule in order to achieve rate enhancement of a chemical reaction of the molecule. In the case of stoichiometric rate enhancement, the concentration of the stoichiometric antibodies is equivalent to the concentration of the target molecules. The skilled artisan will appreciate that the conditions suitable for complex formation can vary depending on the particular molecule and antibody under consideration. Accordingly, the methods of this invention may be practiced under a variety of reaction conditions, in vivo and in vitro, as long as the antibodies are not prevented from complexing with the molecules or otherwise rendered inactive. More specifically, suitable conditions for complex formation encompass solution phase and emulsion reaction systems including a variety of solvents and solvent systems, maintained at a pH value between about 6.0 and about 9.0, preferably between about 6.0 and about 8.5 and at a temperature from about 4° C. to about 50° C., preferably from about 20° C. to about 45C. One of ordinary skill in the art will realize that the choice of solvent will depend on the type of reaction. For example, aqueous solvents are desirable for peptide bond cleavage while non-aqueous solvents can be used to achieve peptide bond formation.

$$\text{The ionic strength}, = \frac{1}{2} \sum_i c_i z_i^2,$$

where c is the concentration and z is the electronic charge of an ionic solute, should be maintained at a value below about 2.0 (ionic strength units), preferably between 0.1 and 1.5. The method of this invention can be carried out at reduced or elevated pressure, but advantageously is practiced at ambient pressure. In addition to solution phase and emulsion reaction systems, suitable conditions also include the use of solid support materials to which the antibody is attached. Such solid support materials are well-known to those of ordinary skill in the art as are methods for attaching antibodies to them.

A specific embodiment of the invention is directed to an extract of blood serum comprising an autoantibody to vasoactive intestinal peptide (VIP). VIP is a 28 amino acid peptide originally isolated from the intestine but now recognized to be a neuropeptide widely distributed in the central and peripheral nervous systems. There is evidence that VIP is a neurotransmitter in its own right. In addition, VIP may modulate neurotransmission by classical transmitters and has been implicated in regulation of blood pressure, bronchial tone, neuroendocrine activity and exocrine secretion. VIP appears to be the major neurobronchodilator in humans and a diminished influence of VIP on the airways may permit a dominance of constrictor influences, and may underlie airway hyperactivity in asthma.

VIP belongs to a family of structurally related peptides, other prominent members of which are peptide histidine isolucine (PHI), growth hormone releasing factor (GRF) and secretin. Like the peptides themselves, there is evidence that the receptors for VIP, GRF, PHI and secretin are related. Receptors for VIP are found in lung, vascular smooth muscle, brain, pancreas, skin, intestine and other tissues. The amino acid sequence of VIP is as follows:

H S D A V F T D N Y T R L R K Q M A V K Y W L N S I L
N—NH$_2$

Antibodies specific to VIP were sought in human subjects. These subjects were 98 healthy humans evaluated by a negative history for illnesses likely to interfere with the studies, who were divided into groups of those diagnosed as having asthma, and those not having asthma. The subjects were identified by code number, and specific antibodies of interest purified from the blood of these subjects are identified herein by the code number of the subject from whom the antibody was purified (e.g. subject 39, subject 5960 and so forth).

It has been discovered that VIP binding antibodies exist in human circulation (6–8). Immunoprecipitation with anti-human IgG as well as chromatography on DEAE-cellulose, gel filtration columns and immobilized protein-G indicate that the plasma VIP binding activity is largely due to IgG antibodies. The antibodies to VIP are present in the blood of 18% of asthma patients and 30% of healthy subjects with a history of habitual muscular exercise, compared to only 2% of healthy subjects with no such history. The antibodies are highly specific for VIP, judged by their poor reaction with peptides related to VIP (i.e., porcine peptide histidine isoleucine (PHI), rat growth hormone releasing factor (GRF), and secretin). A clear difference in the VIP binding affinity of the antibodies from asthma patients (mean $K_{bind}$=0.13 n) and healthy subjects (mean $K_{bind}$=7.7 n) was observed - the antibodies from the asthmatics exhibiting a 60-fold greater binding affinity The range of $K_8$ values of antibodies in asthma patients (0.25 to 26.2 nM$^{-1}$) is similar to that of VIP receptors in the lung. The immune IgG from asthma patients reduces the binding of VIP by lung receptors as well as the VIP-responsive synthesis of cyclic AMP in lung membranes. Thus, the antibodies can be directed against an epitope(s) that binds the receptor or maintains the receptor-binding epitope in an active conformation.

These antibodies are detected by measuring their binding to porcine 1MI-VIP. Human and porcine VIP are structurally identical (9). Thus, the porcine VIP-reactive antibodies found in asthma patients are autoantibodies. It had been observed that diabetics positive for plasma VIP-antibodies had been treated with insulin contaminated with VIP, suggesting that the formation of antibodies was related to the VIP contaminant (10). However, the VIP antibodies in accordance with the invention are naturally occurring, i.e., not elicited by specific immunization against a target antigen.

The antigenic stimulus leading to formation of these autoantibodies cannot be identified with certainty. Candidate stimuli include exposure to viral determinants similar in sequence to VIP [e.g., Peptide-T, an epitope found on the human immunodeficiency virus (21)] and dietary ingestion of avian fish and turtle VIP known to be structurally different from human VIP (22). Muscular exercise, which results in increased plasma VIP immunoreactivity (7, 23), could also be a potential stimulus for VIP autoantibody formation. Indeed, asthma and muscular exercise appear to be associated with an increased incidence of autoantibodies directed against VIP.

Irrespective of the type of antigenic stimulation leading to VIP-autoantibody formation, these antibodies may produce important biologic changes. The range of $K_8$ values observed for the autoantibodies of asthma patients is similar to that reported for VIP receptors present in the lung and other tissues (11), and these antibodies neutralize VIP receptor binding. It is possible that VIP-autoantibodies found in asthmatics neutralize the effect of VIP in the airways.

It has now been discovered that VIP-autoantibodies derived from a human subject ("subject #39") catalyze the hydrolysis of VIP between amino acid residues 16 and 17, i.e. between glutamine and methionine. Kinetic data (FIG. 1) obtained by measuring antibody mediated degradation of mono ($^{125}$I-Tyr$^{10}$)-VIP as a function of increasing concentration of unlabeled VIP indicate (i) the degradation conforms to Michaelis-Menten kinetics, and (ii) the $K_m$ is in the nanomolar range (37.9 nM). A turnover of 0.26 sec$^{-1}$ (i.e., about 16 molecules of VIP are hydrolyzed by one molecule of antibody per minute) was calculated. This calculation is based on the total number of antibodies which are capable of binding to VIP. However, in reality, not all antibodies capable of binding to VIP are necessarily capable of catalytic hydrolysis of VIP. Therefore, the actual turnover number is probably greater than that calculated. Mono($^{125}$I-

Tyr[10]-VIP binding studies by the IgG at 4° C. in radioimmunoassay buffer indicated that hydrolysis of the peptide is undetectable under these conditions. A linear Scatchard plot (FIG. 2A) and a Hill slope close to unity (FIG. 2B) suggested a single type of antibody with $K_d$ 0.4 nM and concentration of 73.4 fmoles/mg IgG, or about 0.001% of the total IgG (assuming antibody bivalency).

The $k_{cat}$ and $k_{cat}/k_m$ values for the hydrolysis were 0 26 sec$^{-1}$ and $6.9 \times 10^6 M^{-1} sec^{-1}$, indicating that anti-VIP acts catalytically to hydrolyse VIP. The VIP hydrolytic activity in the IgG fraction is precipitated by ammonium sulfate, is inhibited by antiserum against human IgG, and exhibits the characteristic of authentic IgG when chromatographed on DEAE-cellulose, immobilized protein-G and high performance gel filtration columns.

That the hydrolysis of VIP is caused by anti-VIP autoantibodies and not by a contaminating protease is clear from the findings that (i) the IgG did not contain non-immunoglobulin material; (ii) the Fab fragment of IgG exhibited a molecular mass close to 50 kDa and it hydrolysed VIP; (iii) the hydrolytic activity of intact IgG was retained on immobilized protein G, and then released by low pH treatment; (iv) the IgG revealed a single peak of hydrolytic activity with a molecular mass close to 150 kDa; (v) of the original VIP hydrolytic activity present in IgG purified by DEAE-cellulose chromatography, 78% and 80% was preserved in the retentate after ultrafiltration on a 100 kDa cutoff filter and in the ammonium sulfate precipitable fraction, respectively; (vi) treatment of the IgG preparation with anti-human IgG and removal of the immunoprecipitate decreased the hydrolytic activity by 75%; (vii) only two of six immune IgG preparations showed hydrolytic activity, and nonimmune IgG was without activity, (viii) the observed $K_m$ value suggests hydrolysis of VIP by a relatively tight binding agent, such as an antibody; (ix) the Gln-Met bond hydrolyzed by the antibody has not been described as a target for enzymatic (peptidase) hydrolysis; (x) it is believed that tight association of protease with IgG has not been described; and (xi) the only IgG binding factors in literature are the cell surface receptors for immunoglobulins (24) and intracellular regulators of IgG secretion (25).

The hydrolytic activity of anti-VIP catalytic autoantibody 39 is latent because of the presence of a tightly bound, relatively small sized molecule. This latency was based on the discovery that little or no VIP hydrolytic activity was present in the IgG fraction of serum isolated from individuals having the anti-VIP catalytic autoantibody when the IgG was tested for hydrolytic activity directly after purification on immobilized protein G (27). However, VIP hydrolytic activity was observed when the IgG was subjected to any of the following treatments: (a) extensive dialysis; (b) two cycles of ultrafiltration; (c) prolonged washing of the IgG at neutral pH when bound on protein G-Sepharose; or (d) affinity chromatography on a VIP-Sepharose column.

The binding of an antigen (or an inhibitor) to an antibody is an equilibrium reaction as follows:

Antibody +

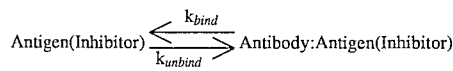

$$\text{Antigen(Inhibitor)} \underset{k_{unbind}}{\overset{k_{bind}}{\rightleftharpoons}} \text{Antibody:Antigen(Inhibitor)}$$

Treatments (a)–(d) remove unbound inhibitor forcing the equilibrium to the left ($k_{unbind}$) and facilitating further removal of inhibitor, and thereby leaving behind hydrolytically active antibody.

A second human subject ("subject #5960") has been identified as producing a catalytic anti-VIP autoantibody capable of cleaving seven different peptide bonds. The 5960 catalytic autoantibody was purified by the methods described above for the number 39 catalytic autoantibody. The bonds cleaved by the number 5960 catalytic autoantibody are between the residues: Arg[14]-Lys[15], Gln[16]-Met[17], Met[17]-Ala[18], Ala[18]-Val[19], Lys[20]-Lys[21], Lys[21]-Tyr[22] and Thr[7]-Asp[8] as illustrated by FIG. 13B.

A third human subject ("subject #80) has been identified as producing a catalytic autoantibody capable of cleaving 5 different bonds. The bonds cleaved by the #80 catalytic autoantibody are between the residues: Gln[16] and Met[17], Met[17] and Ala[18], Ala[18] and Val[19], Lys[20] and Lys[21] and Lys[21] and Tyr[22] as illustrated in FIG. 13.

Peripheral blood lymphocytes from a subject positive for hydrolytic anti-VIP antibodies can be transformed with Epstein-Barr Virus (EBV). The culture supernatant of these EBV transformed lymphoblastoid cells cause hydrolysis of VIP that may be greater than that by supernatants obtained from a control cell line. Thus, it is believed that the hydrolytic VIP antibodies may be produced by the transformed cells.

It is well known that certain diseases are associated with autoantibodies directed against hormones and cell surface antigens. Examples of these diseases and associated autoantibodies are:

| Disease | Autoantibody to |
|---|---|
| Diabetes | Insulin, Insulin receptor |
| Myasthenia gravis | acetylcholine receptor |
| Graves disease | thyroid stimulating hormone receptor |
| Systemic lupus erythematous | small nuclear RNA, DNA, histones |
| Pernicious anemia | Intrinsic factor of Castle, gastric parietal cell antibodies |

Since catalytic autoantibodies are likely to cause more harm than non-catalytic antibodies, it is possible that the autoimmune diseases may be caused by catalytic autoantibodies directed against nucleic acids, key regulatory peptides and proteins (e.g., insulin, glucagon, prolactin, VIP, substance P, blood clotting factors) and the cell surface receptors for these agents. Thus, the methods of the invention provide diagnostic tests which may be used to evaluate whether autoimmune diseases are associated with catalytic autoantibodies directed against specific proteins. For example, asthma may be caused by a deficiency of VIP. Catalytic anti-VIP antibodies could bring about this deficiency. If the presence of catalytic anti-VIP antibodies is detected and established, using the methodologies described herein, in individual asthma subjects, this would help determine the best way to treat the asthma in such subjects.

Autoimmune diseases can be treated in accordance with the invention by administering to an afflicted animal an inhibitor capable of binding to the autoantibody, thereby preventing the autoantibody from catalyzing a chemical reaction of the self-antigen, in particular, cleavage of a peptide bond. The inhibitor can be the self-antigen, an analog of the self-antigen, a small peptide containing an epitope of the self-antigen at which epitope the chemical reaction takes place, an analog of a small peptide containing the epitope, or a small peptide containing an analog of the epitope. The inhibitor is administered, in combination with a suitable pharmaceutical carrier, either orally or by injection (I.V. or I.M.).

In addition, autoantibody catalyzed cleavage of peptide bonds is likely to inactivate the target protein substrate, the peptide bond cleavage is likely to be highly specific, and, by definition, a single catalytic autoantibody molecule inactivates multiple substrate molecules. Inactivation by catalytic autoantibodies of proteins important in cancer, infectious diseases and hormonal or neural disorders forms the basis for catalytic autoantibody based therapies in accordance with the invention. For example, such target proteins include molecules that are found in or stimulate the growth of cancer cells (oncogene products, growth factors, carcinoembryonic antigens). Many tumors produce VIP and this peptide stimulates growth of some tumors. Catalytic anti-VIP autoantibodies may provide a cure for these tumors. A segment of the gp120 coat protein of HIV shares structural similarity with VIP(7-11) (Peptide-T). Catalytic anti-VIP antibodies directed against Peptide-T may be effective in treating HIV infections.

The invention will be more fully described and understood with reference to the following examples which are given by way of illustration.

EXAMPLE 1

Preparation of Mono($^{125}$I-Tyr$^{10}$) -VIP

Figure 3:
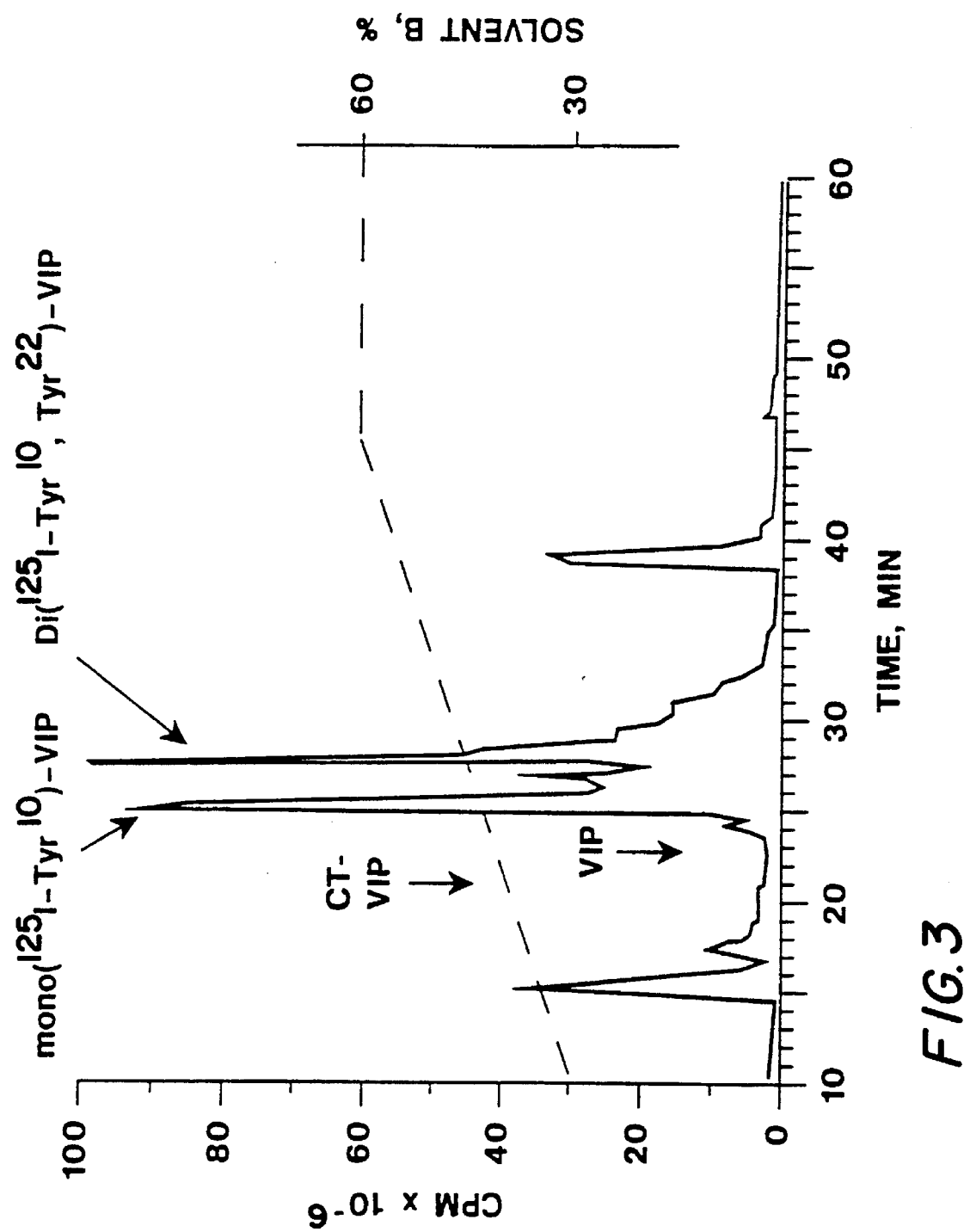
FIG. 3 shows the separation of mono ($^{125}$I, Tyr$^{10}$)-VIP and di($^{125}$I, Tyr$^{10}$, Tyr$^{22}$)-VIP by reverse phase HPLC.

Purified porcine VIP (Bachem) was labeled with $^{125}$ iodine by the chloramine-T method (21). The resulting mono (125I-Tyr° )-VIP was purified on a Seppak C18 cartridge followed by reverse phase HPLC with a gradient of acetonitrile in trifluoroacetic acid(12). Two major peaks of radioactivity were obtained (FIG. 3), corresponding to compounds that reacted with rabbit anti- VIP antiserum in radioimmunoassay. In order to obtain sufficient peptide for sequencing, VIP was iodinated with $^{25}$I diluted with $^{127}$I to reduce the specific activity, and purification performed as before. Analysis of the peak with retention time 25.3 min on an Applied Biosystems sequenator with on-line phenylthiohydantoin amino acid detection showed radioactivity mainly in cycle 10, with HPLC characteristics similar to those of monoiodotyrosine (purchased from Calbiochem), indicating that this material was mono($^{125}$I-Tyr$^{10}$)-VIP. The second peak of radioactivity (retention time 27.8 min) was identified as di($^{125}$I-Tyr$^{10}$,Tyr$^{22}$)-VIP by similar methods. The di($^{125}$I- Tyr$^{10}$,Tyr$^{22}$)-VIP and mono($^{125}$I-Tyr$^{10}$)-VIP performed nearly equivalently in a radioimmunoassay test. Since native VIP, VIP oxidized with chloramine-T without Na$^{125}$I(CT-VIP) and mono ($^{125}$I,Tyr$^{10}$)-VIP were well separated, it was concluded that the $^{125}$I-VIP was free of unlabeled peptide.

EXAMPLE 2

Demonstration Of VIP Autoantibodies In Human Subjects

The antibodies were measured in plasma samples from asthma patients and healthy subjects, subdivided into high exercise (Hx) and low exercise (Lx) subgroups (7). Asthma was diagnosed on the basis of patient history and typical clinical indicators. The healthy Hx subjects had a history of habitual muscular exercise, and the healthy Lx subjects did not. Human blood samples were collected in a mixture of peptide hydrolase inhibitors (aprotinin, phenylmethylsulfonyl fluoride, pepstatin, ethylene diamine tetracetic acid)(7, 8). The immunoglobulin G (IgG) fraction from blood was prepared by sequential chromatography (6,8) on DEAE-cellulose (Whatman, Inc. Clifton, N.J.) and protein G-Sepharose (Pharmacia, Fine Chemicals, Piscataway, N.J.). The IgG (4 mg/ml) was ultrafiltered on a YM-10 membrane having an average cut off molecular weight of 10,000 Daltons using an Amicon Model 8 MC apparatus to 27 mg/ml, diluted back to 0.8 mg/ml and then subjected to a second cycle of ultrafiltration. The final concentration of IgG prepared in this manner was about 20 mg/ml. Electrophoretic analysis and staining of nitrocellulose blots with anti-human IgG conjugated to peroxidase did not reveal presence of non-immunoglobulin material in this preparation (Example 8). The presence of VIP-antibodies was established by measuring saturable binding of mono($^{125}$I-Tyr$^{10}$)-VIP (binding inhibited by excess unlabelled VIP) in plasma samples or purified IgG (7,8). The monoiodinated form of VIP was used because it is more likely to reproduce the interactions of native VIP with the antibodies. Plasma samples with %B/T values (where B and T are cpm saturable binding and total $^{125}$I-VIP, respectively) greater than %5 (approximately 1500 cpm) were considered positive for the VIP-binding antibody. Bound and free VIP were separated by precipitation with polyethylene glycol (7) or specific sheep antibodies against human IgG (8). Plasma samples from some asthma patients and healthy subjects were observed to exhibit saturable $^{125}$I-VIP binding activity (up to 67.5% of total $^{125}$I-VIP) (8). The VIP-antibodies were found in 18% of asthma patients (N=74), 30% of healthy Hx subjects (N=51), 2% of healthy Lx subjects (N=44). The mean $^{125}$I-VIP binding values (% B/T with SEM in parentheses) in the antibody positive asthma and Hx subjects were 23.4 (5.3) and 20.4 (3.2). The lone antibody positive subject in the Lx group showed a % B/T value of 12.1%.

EXAMPLE 3

Determination That VIP-Antibodies Are Predominantly Of The IgG Class

A specific goat anti-human IgG serum precipitated 83.7% +−5.1% (mean +−S.E.M.) and 79.0% +−4.5% of the VIP binding activity present in the 13 asthma and 16 non-asthmatic subjects, respectively (7). Goat anti-human IgM antibodies did not precipitate the VIP-binding activity in any of the plasma samples tested (N=16). The plasma VIP binding activity coeluted with authentic human IgG from DEAE-cellulose and gel filtration columns, and, pepsin treatment produced a F(ab)$_2$ fragment with VIP-binding activity. The binding activity was bound by immobilized protein G, an agent that binds IgG via the Fc portion of the molecule, and was released by treatment at low pH.

EXAMPLE 4

The Autoantibodies in Asthmatics Have a Higher VIP Binding Affinity Than Those in Healthy Individual Binding affinities of the antibodies present in seven asthma patients and eight non-asthmatic subjects were determined (7,8). Apparent $K_a$ (affinity constant) of the antibodies and binding capacities were obtained by computer assisted analysis of the displacement of (Tyr$^{10-125}$I)VIP binding by increasing unlabeled VIP concentrations. Scatchard plots were linear, or were resolved into two linear components, suggesting the presence of one or two classes of antibodies, respectively. The mean $K_a$ values for the high affinity autoantibodies of asthmatic (n=7) and non-asthmatic subjects (n=8) were 7.8×10$^9$ M$^{-1}$ and 0.13×10$^9$ M$^{-1}$ (P<0.005), t-test) and their VIP (in pmol VIP/ml plasma) were 0.58±0.05 and 55.7±39.2, respectively. The mean $K_a$ values for the low affinity antibody of asthmatic (n=5) and non-asthmatic subjects (n=3) were similar (0.04×$^9$ M$^{-1}$ and 0.08×10$^9$ M$^{-1}$, respectively; P>0.05). The VIP-binding capacities (mean) for the low affinity antibodies of asthmatic and non-asthmatic subjects were 24.7 and 152.6 pmol/ml, respectively. These data indicated that the affinity of VIP-antibodies present in asthma patients (mean $K_a$ 7.8×10$^9$ M$^{-1}$)

was substantially greater (by 60-fold) than that of the antibodies in healthy subjects.

EXAMPLE 5

Determination Of Autoantibody Specificity For VIP

Porcine peptide histidine isoleucine (PHI), rat growth hormone releasing factor (GRF) and secretin, peptides partially identical to VIP in their amino acid sequence, were employed to examine the specificity of the antibodies (7,8). These peptides (1 µM) did not significantly displace the $^{125}$I--VIP binding by plasma from six asthma patients and four non-asthmatic subjects (8). The plasma antibodies in one asthmatic and one nonasthmatic subject showed partial reactivity with PHI, GRF and secretin (21.9% to 33.4%). The poor reaction of the antibodies with PHI, GRF and secretin suggests their high level of specificity for VIP.

EXAMPLE 6

Hydrolysis Of VIP By Anti-VIP Autoantibodies

To compare antibody mediated hydrolysis and spontaneous hydrolysis of the peptide VIP, mono($^{125}$I-Tyr$^{10}$)-VIP was incubated with (i) immune and (ii) nonimmune IgG for increasing lengths of time. IgG from a nonimmune human subject and a VIP antibody positive subject was prepared by chromatography on DEAE cellulose followed by ultrafiltration as described in Example 2. The IgG or assay diluent (final volume of 200 µl 50 mM Tris-HCl, 100 mM glycine, 0,025% Tween-20 and 0.1% bovine serum albumin, pH 8.0) was incubated with mono ($^{125}$I,Tyr$^{10}$)-VIP (approximately 30 p) for increasing lengths of time at 38° C. Bovine serum albumin and Tween-20 were included in these incubations to prevent adsorptive loss of the mono ($^{125}$I,Tyr$^{10}$)-VIP on glass and plastic surfaces. Precipitation with trichloroacetic acid (TCA) (13) was used as the initial criterion of mono($^{125}$I,Tyr$^{10}$)-VIP degradation. Accordingly, 1 ml of TCA (final concentration 10% v/v) was added to the reaction mixtures which were then centrifuged at 3000× g. The supernatants were aspirated and the radioactivity was measured in the pellets (Beckman model 5500 spectrometer). At this TCA concentration, greater than 90% of intact mono ($^{125}$I,Tyr$^{10}$)-VIP was precipitated (i.e., found to appear in the TCA-insoluble pellet). Values for VIP hydrolysis were computed from the radioactivity observed as counts per minute (CPM) in the TCA-precipitable fractions as:

(CPM$_{assay\ buffer}$- CPM$_{antibody}$) ×100/CPM$^{assay\ buffer}$. Compared to 8% hydrolysis of the mono ($^{125}$I,Tyr$^{10}$)-VIP incubated with nonimmune IgG, 73% of the peptide was hydrolyzed by treatment with immune IgG.

The ability of the IgG to hydrolyze mono-($^{125}$I,Tyr$^{10}$)-VIP was not lost by precipitation with 50% saturated ammonium sulfate or ultrafiltration on a 100 kDa membrane filter. Treatment of the IgG with rabbit anti-human IgG or treatment at 100° C. (10 min) prior to incubation with mono ($^{125}$I,Tyr$^{10}$)-VIP destroyed the hydrolytic activity of the IgG as indicated by a reduction in the amount of radioactivity in the peak with RT of 10 min.

Figure 4:
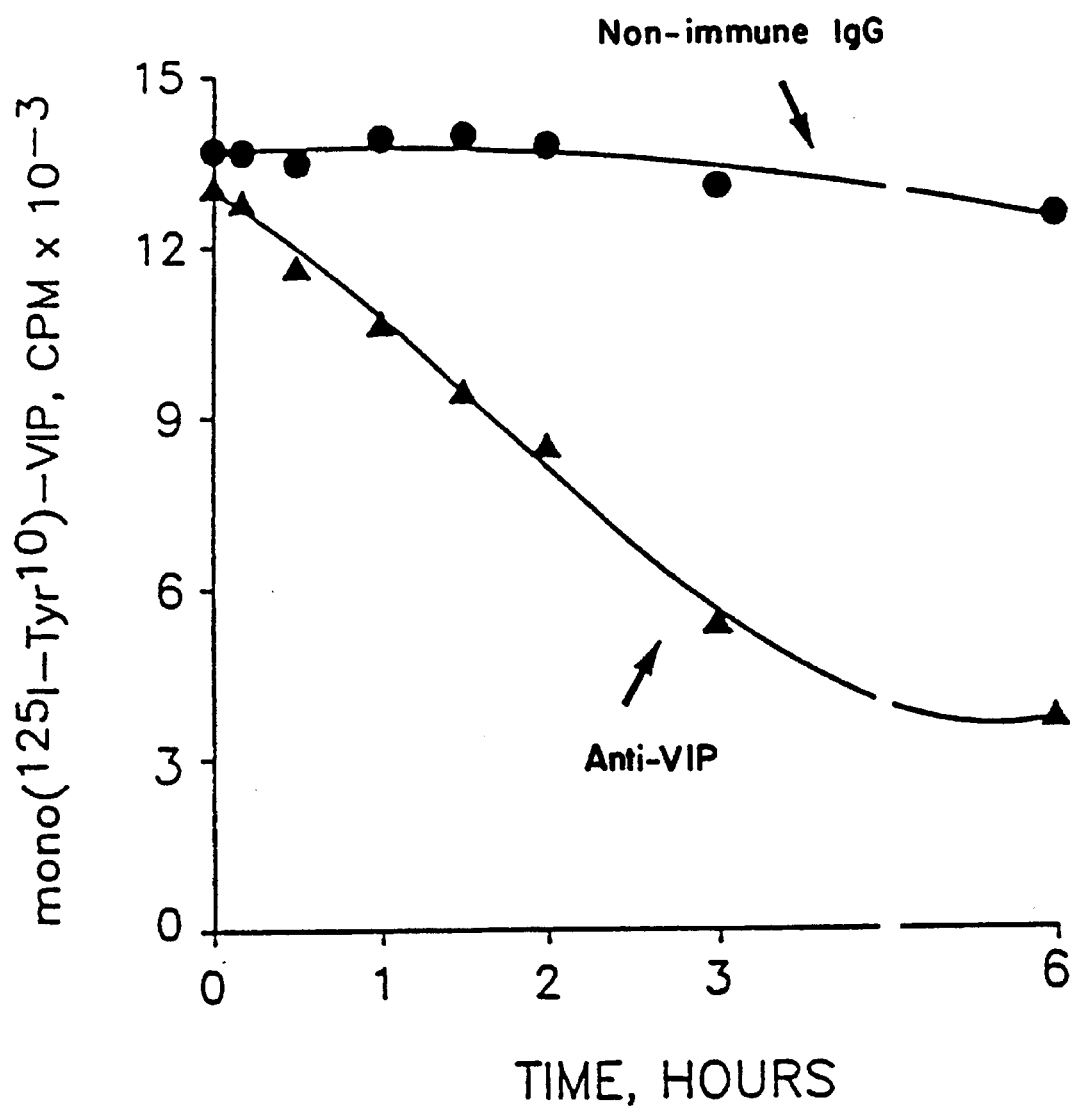
FIG. 4 shows reduced precipitation of mono($^{125}$I, Tyr$^{10}$)-VIP treated with 42.5 µg of the anti-VIP antibody fraction (▲) as compared to an equivalent concentration of a non-immune antibody fraction (●) (the starting radioactivity in each tube was 15,040 CPM)

Treatment of mono ($^{125}$I,Tyr$^{10}$)-VIP with immune IgG for increasing time periods progressively reduced the amount of radioactivity precipitated by 10% TCA, as shown in FIG. 4. After incubation with immune IgG for 6 h, 73% of the starting mono ($^{125}$I,Tyr$^{10}$)-VIP was no longer precipitated by TCA, compared to only 8% of the mono ($^{125}$I,Tyr$^{10}$)-VIP incubated with nonimmune IgG. The degradation of mono ($^{125}$I-Tyr$^{10}$)-VIP was pH dependent, with an optimum pH of 8.0–9.0.

Figure 2A:
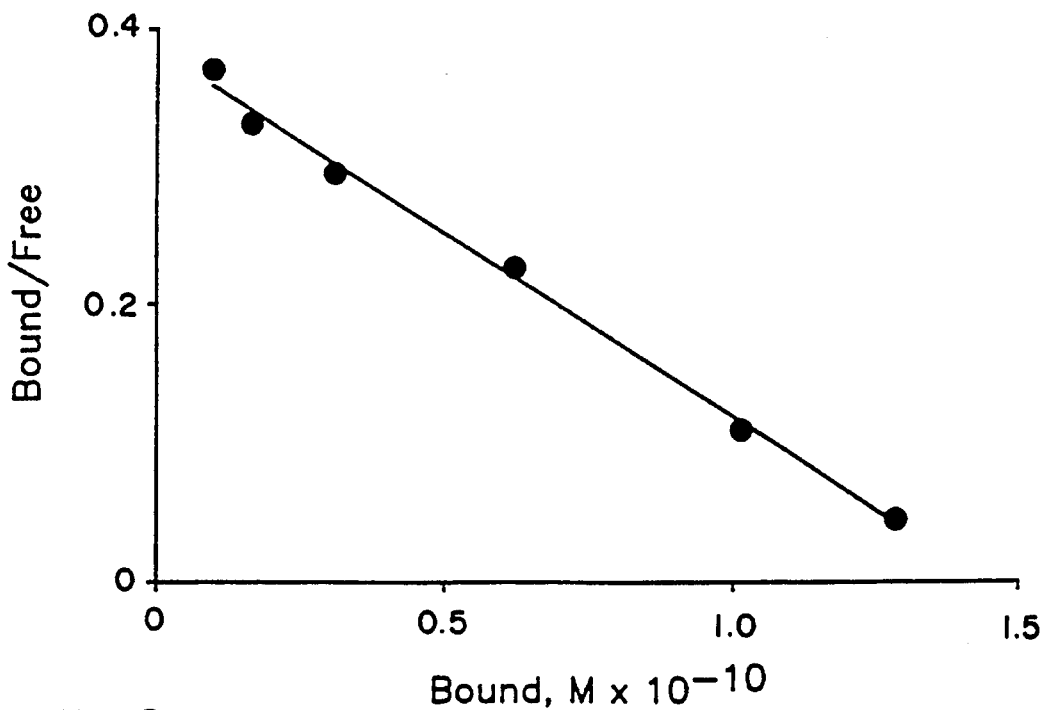

Kinetic data were obtained by incubating IgG with increasing concentrations of unlabeled VIP mixed with a fixed concentration of mono ($^{125}$I,Tyr$^{10}$)-VIP as trace for 2 h at 38° C. The hydrolysis was saturable with increasing VIP concentrations and a plot of 1/velocity vs. 1/substrate concentration was linear, as shown in FIG. 1, indicating that the reaction conformed to Michaelis-Menten kinetics. A $K_m$ for the reaction of 37.9 nM, determined from the slope of the linear plot in FIG. 1, indicated relatively stable antibody-VIP binding. A Scatchard plot of VIP binding by the antibody, under conditions that did not lead to VIP hydrolysis (see Example 9), was linear, as shown in FIG. 2A. The slope for the Hill-plot, shown in FIG. 2B, was close to unity (1.02). These data indicated a single antibody class with $K_d$ 0.4 nM and concentration 73.4 fmol/mg IgG (assuming antibody bivalency). The $k_{cat}$ and $k_{cat}/K_m$ values for the hydrolysis, computed on the basis of the kinetics of hydrolysis and the antibody concentrations obtained from the binding data, were 0.26 sec$^{-1}$ and 6.9×10$^6$M$^{-1}$sec$^{-1}$. These values indicated that the anti-VIP acts catalytically to hydrolyse VIP. A turnover of 0.26 sec$^{-1}$ (i.e., about 16 molecules of VIP are hydrolyzed by one molecule of antibody per minute) was calculated. This calculation was based on the total number of antibodies which were capable of binding to VIP. However, in reality, not all antibodies capable of binding to VIP are necessarily capable of catalytic hydrolysis of VIP. Therefore, the actual turnover number is probably greater than that calculated.

EXAMPLE 7

Identification of Peptide Fragments Resulting From Hydrolysis of VIP Catalyzed by Anti-VIP Autoantibodies from Subject #39

Figure 5:
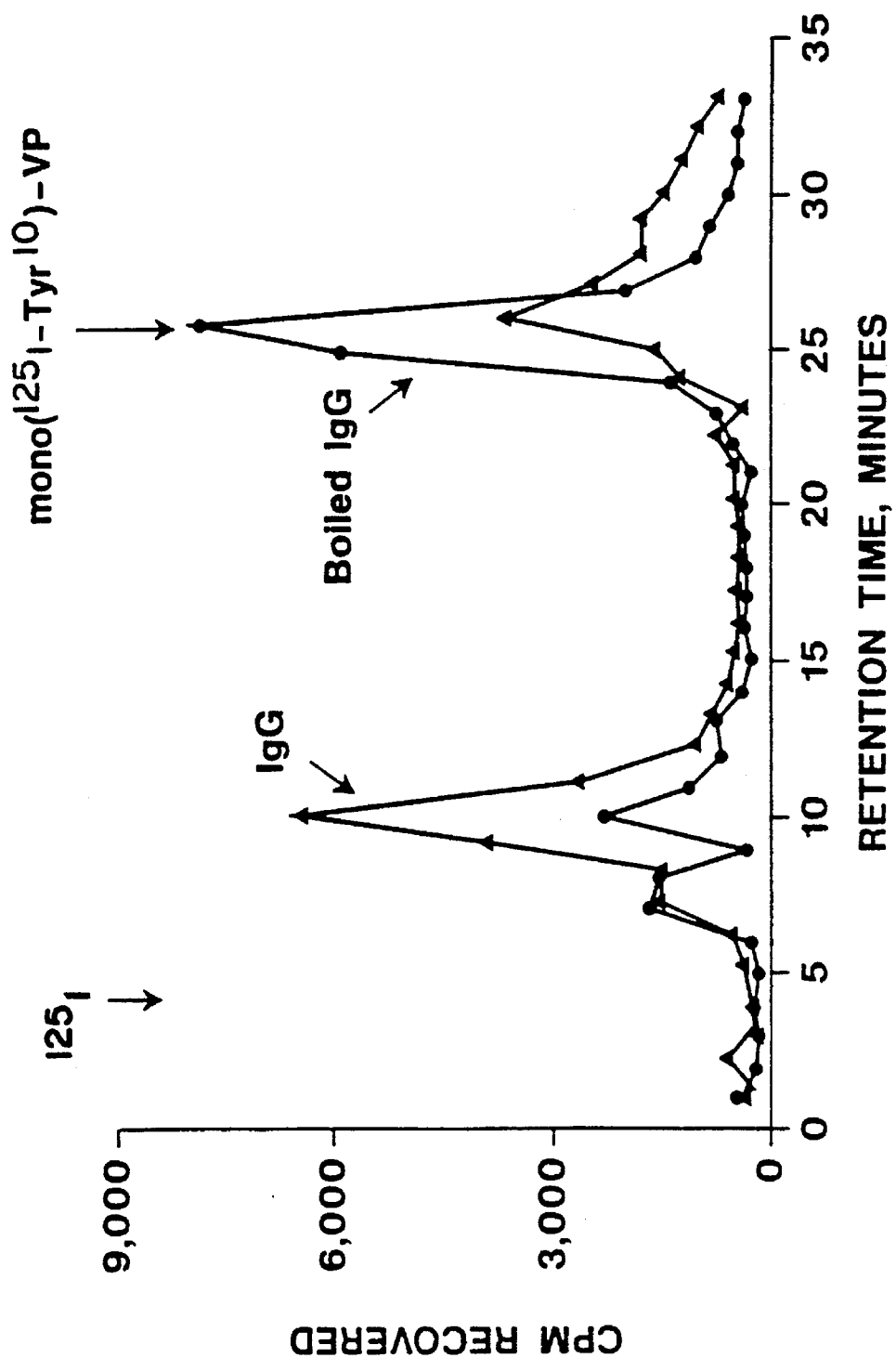
FIG. 5 shows the reverse phase HPLC of mono ($^{125}$I, Tyr$^{10}$)-VIP treated with intact IgG or IgG boiled for ten minutes.
Figure 6:
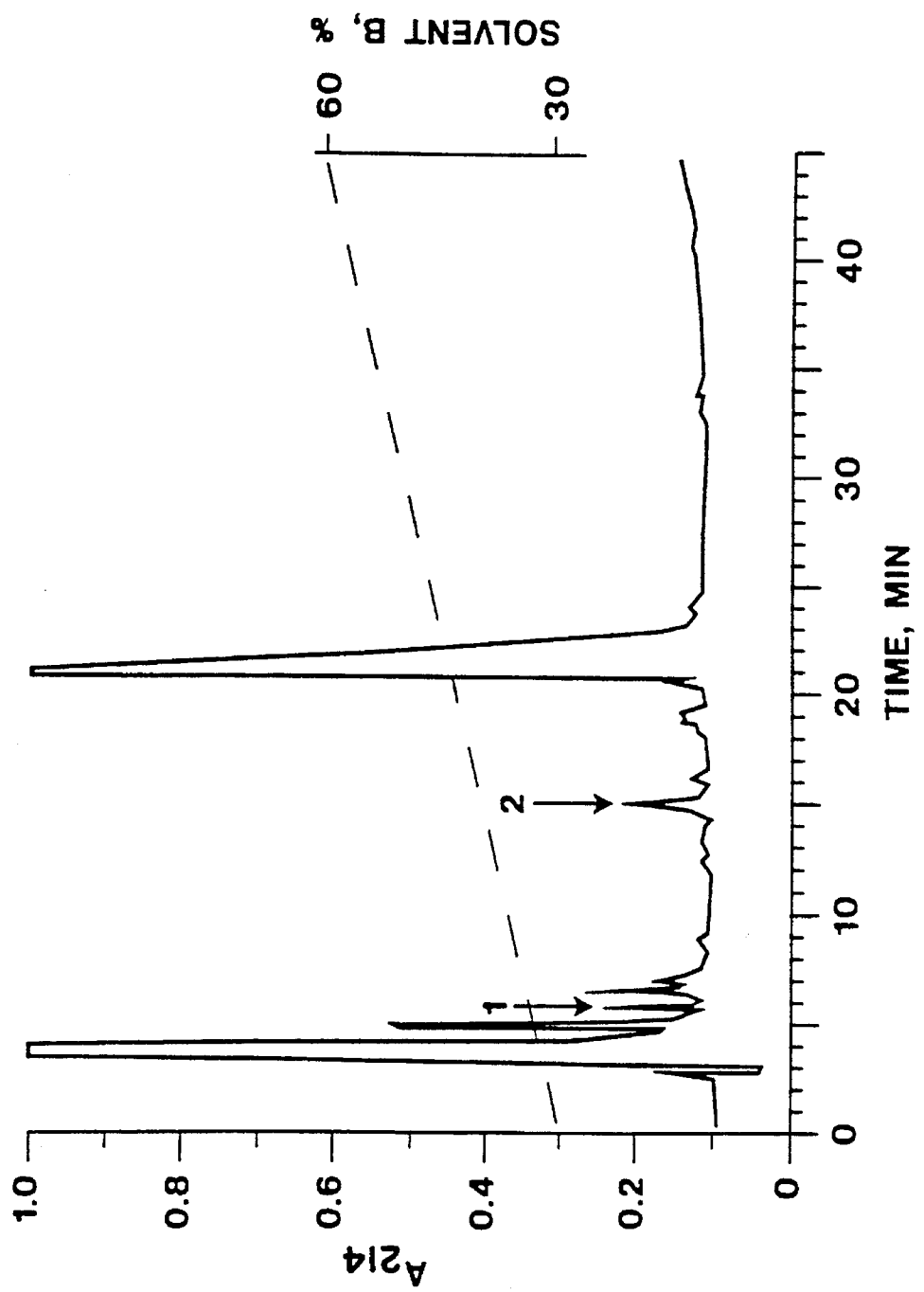
FIG. 6, 7 and 8 show reverse phase HPLC purification of VIP fragments produced by treatment with the anti-VIP antibody fraction.
Figure 7:
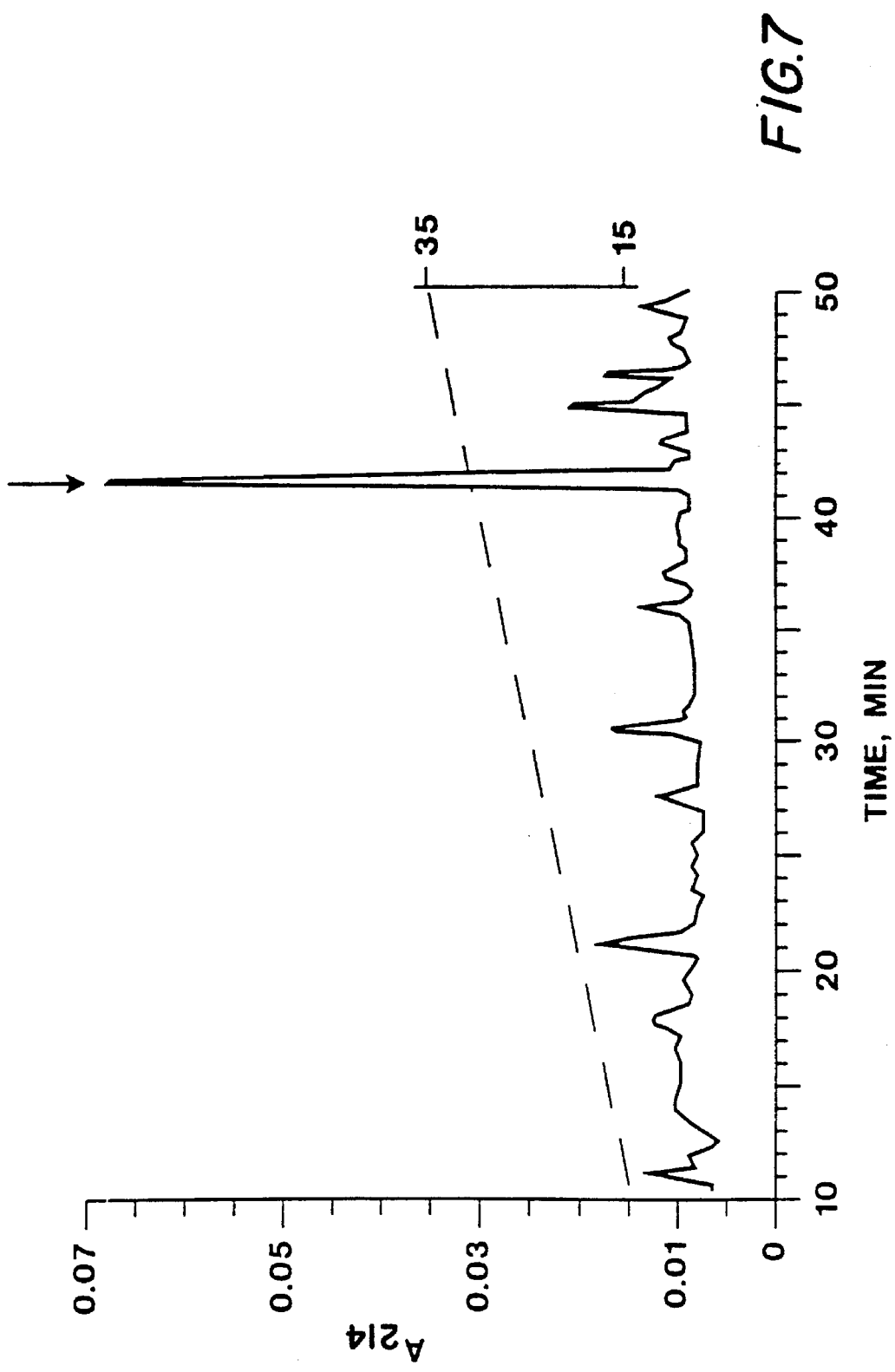
Figure 8:
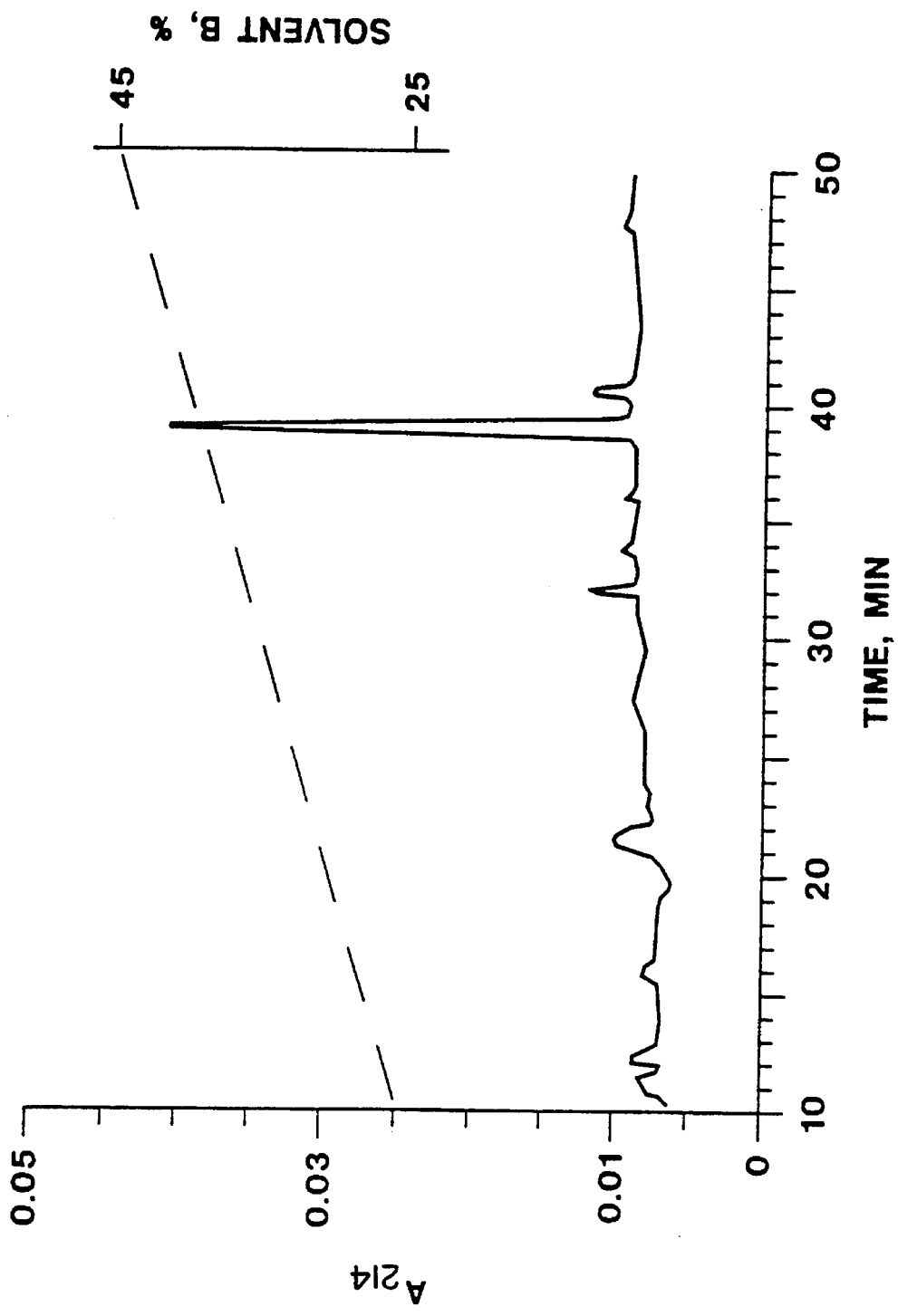
Figure 9:
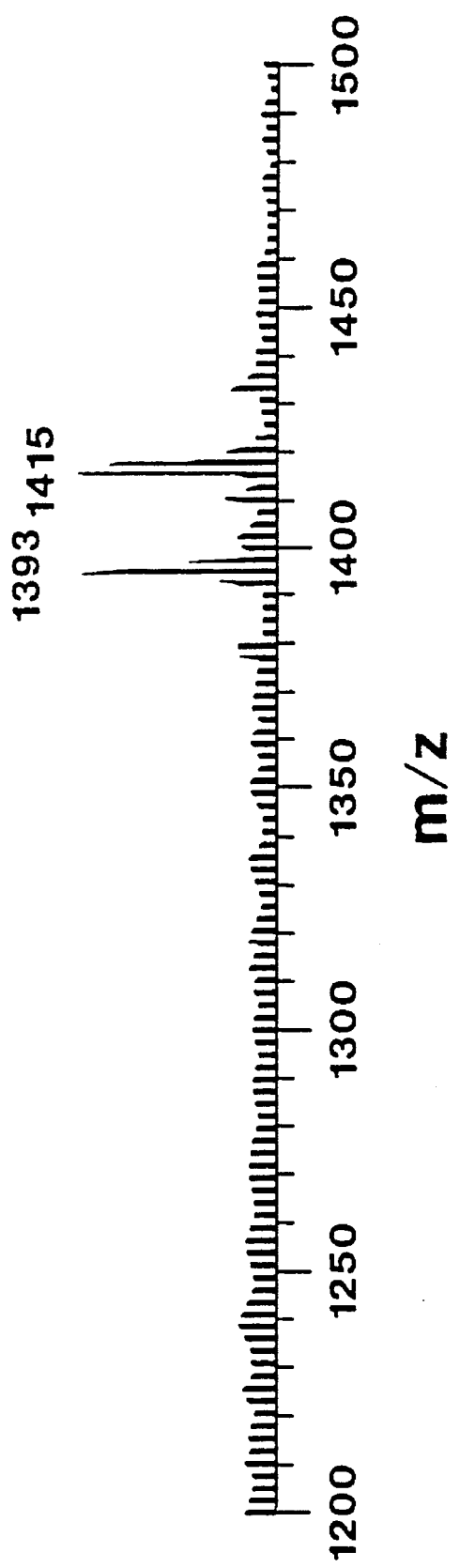
FIG. 9 shows a partial positive ion fast atom bombardment-mass spectrum (m/z 1200–1500) of the VIP fragment (2) purified in FIG. 8.

Reverse phase HPLC of mono ($^{125}$I-Tyr$^{10}$)-VIP treated with the immune IgG from subject #39 revealed a reduction in the amount of intact mono ($^{125}$I, Tyr$^{10}$)-VIP (retention time (RT):25 min.)and the appearance of an early eluting peak of radioactivity (RT:10.0 min) that was well separated from intact mono (($^{125}$I-Tyr$^{10}$)-VIP and free $^{125}$I (RT:65–7.0 min) (FIG. 5). Heat treatment of the IgG prior to incubation with mono(Tyr$^{10}$,$^{125}$I)-VIP resulted in a reduction in the amount of radioactivity in the peak with RT 10 min When mono ($^{125}$I, Tyr$^{10}$))-VIP was incubated in buffer instead of the IgG, the bulk of the radioactivity was recovered in the form of intact peptide and only 13.9% in the peak with RT of 10 min. In order to purify the fragments of VIP, unlabelled VIP (50 µg) was treated with 525 µg immune IgG or nonimmune IgG as before, except that bovine serum albumin was omitted from the reaction mixture. The reaction mixtures were extracted on Extract Clean C18 cartridges (Alltech), and then subjected to reverse phase HPLC on a Novapak-C18 column (Waters), eluting with a gradient of acetonitrile in trifluoroacetic acid. The absorbance of the eluate was monitored at 214 nM. Two $A_{214}$ nm absorbing peaks (labeled 1 and 2 in FIG. 6), noted after treatment of the VIP with immune IgG, were absent in peptide preparations treated with nonimmune IgG or assay buffer. These peaks were purified by a second round of reverse phase HPLC using shallower gradients for elution (FIG. 7 and 8). The peptide fractions purified by reverse phase HPLC were dried, and sequenced using an Applied Biosystems pulsed liquid phase sequenator (model 477A) with on-line phenylthiohydantoin-amino acid detection. This procedure demonstrated unequivocally that the major $A_{214}$ absorbing peaks identified as 1 and 2 in FIG. 7 and 8, respectively, were VIP [1-16] and VIP [17-28]. Fast atom bombardment (f.a.b.)-mass spectrometry of peptide 2 in FIG. 8 and intact VIP[1-28] was performed in the positive ion mode on a VG Analytical ZAB-2SE spectrometer (acceleration potential:8kV)(M-Scan) using peptides dissolved in 5% acetic acid and thioglycerol/glycerol or m-nitrobenzyl alcohol matrices. Mass calibration was performed with cesium iodide or cesium iodide/glycerol. The F.a.b.-mass spectrometric analysis (FIG. 9) suggested that the molecular mass of peptide 2 was 1393 daltons corresponding to the molecular ion of VIP [17-28]. It is believed that the additional peak observed with mass of 1415 daltons probably represented the sodium adduct of VIP [17-28]. Analysis of VIP [1-28] resulted in a signal at 3325 daltons that corresponded well to the molecular ion of the peptide.

EXAMPLE 8

Determination that Anti-VIP Autoantibody (IgG) And Not A Contaminating Peptidase Caused Hydrolysis of VIP IgG Did Not Contain Non-Immunoglobulin Material Overloaded IgG (50 μg) was subjected to electrophoresis in 12–20% polyacrylamide gels. Silver staining revealed one major IgG band and a minor light chain band with molecular mass 150 kDa and 25 kDa, respectively. A nitrocellulose blot of the gel was treated with rabbit anti-human IgG conjugated to peroxidase (Accurate) and stained with diaminobenzidine and hydrogen peroxide. Both bands were reactive with the anti-human IgG, indicating that the IgG did not contain non-immunoglobulin material.

A. VIP-Cleaving Activity Resided In The Fab Fragment

The IgG (10 mg in 0.5 ml) was treated with papain conjugated to agarose (Pierce) (1.5 ml in 20 mM sodium phosphate, pH 7.0, 10 mM EDTA and 20 mM cysteine) for 5 h at 38° C. with vigorous shaking. The mixture was centrifuged, and Fab in the supernatant was purified by chromatography on protein A conjugated to agarose (2.2 ml gel; Pierce). The column was washed with 10 mM Tris-HCl, pH 7.5 to recover unretained Fab. This fraction was concentrated by ultrafiltration on an Amicon YM-10 filter. The Fab fragment prepared in this manner exhibited a molecular mass of 50 kDa. The retentate, the parent IgG fraction and marker proteins (right lane) were electrophoresed on a 8-25% gradient polyacrylamide gel using a Phast system (Pharmacia) and the gel was stained with Coomassie blue, as shown in FIG. 10A. Increasing concentrations of the Fab preparation were incubated with mono ($^{125}$I, Tyr$^{10}$)-VIP in 0.05M Tris-HCl, 0.1M glycine, pH 8.0, containing 0.025% Tween 20 (assay diluent) for 3 h at 38° C. Trichloroacetic acid (TCA) was added to 10% (v/v), the tubes centrifuged (5800× g; 20 min), the supernatants aspirated and radioactivity in the pellets determined as described in Example 5 above. FIG. 10B indicated that the Fab fragment caused dose dependent cleavage of VIP. Thus, the catalytic activity resided in the Fab fragment.

Figure 11:
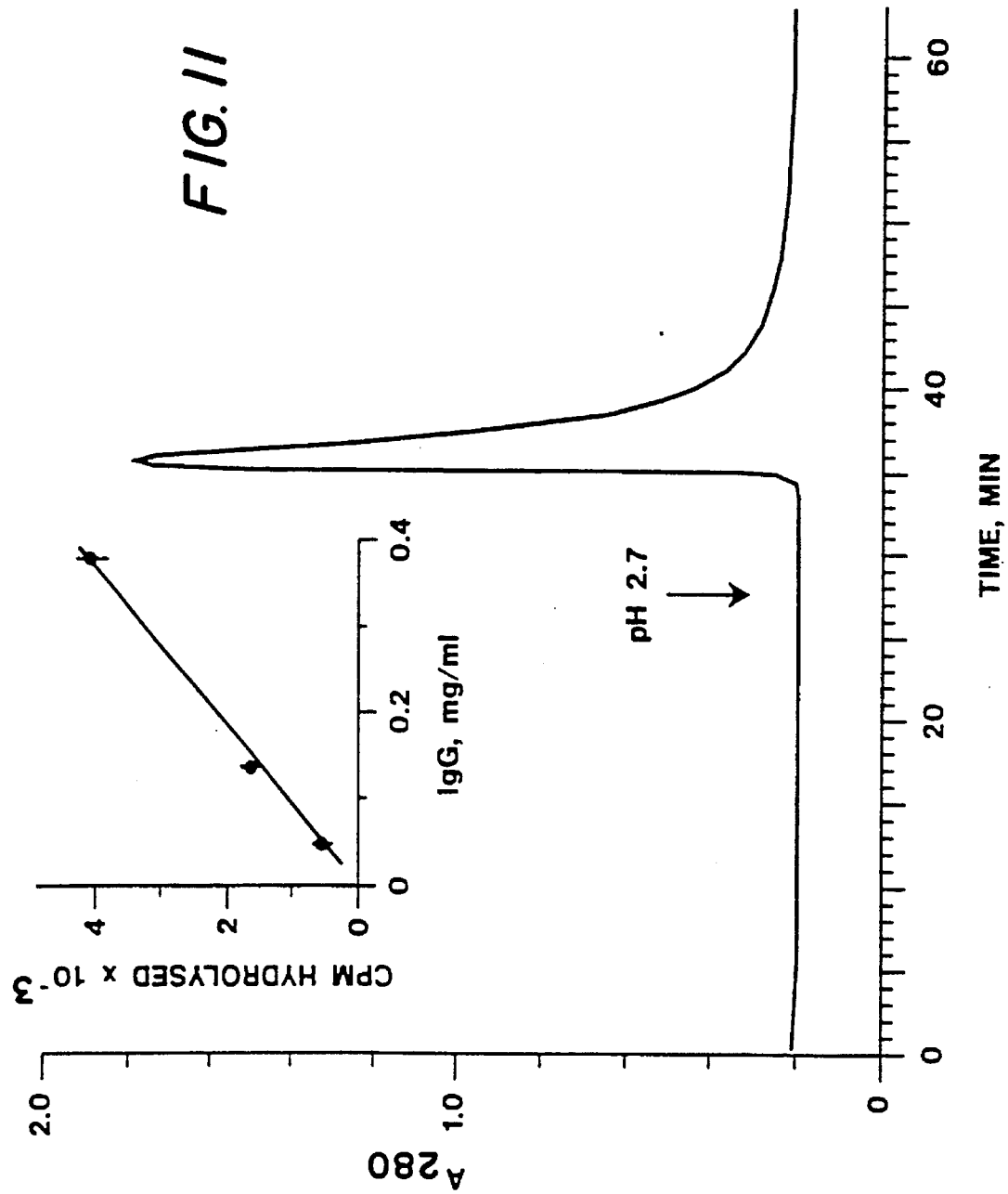
FIG. 11 shows further purification of the VIP-hydrolytic activity by affinity chromatography on Protein G-Sepharose and the results of an assay for VIP-hydrolytic activity (inset)

B. Hydrolytic Activity Of Intact IgG Was Retained On Immobilized Protein G And Was Released By Low pH Treatment IgG purified on a DEAE-cellulose column was chromatographed on protein G conjugated to Sepharose (Pharmacia) in 50 mM Tris-HCl, pH 7.3. Protein G is an agent which binds immunoglobulin at its $F_c$ region. All of the $A_{280}$ was retained by the protein G, and then released upon application of a low pH buffer (0.1 M glycine-HCl, pH 2.7). The eluate fractions were made to pH 8 with 1M Tris-HCl, pH 9, pooled and assayed for VIP hydrolytic activity (inset) as in FIG. 11.

C. IgG Exhibited A Single Peak Of Hydrolytic Activity With A Molecular Mass Close To 150 kDa To determine that hydrolysis took place at a single site on the antibody, the protein G purified IgG was gel filtered on a Superose-12 column (Pharmacia) in 50 m Tris-HCl, pH 8 buffer at a rate of 0.5 ml/min. Marker proteins used for comparative molecular mass determination were ferritin, catalose, bovine serum albumia and chymotrypsinogen. Gel filtration chromatography indicated a single peak of hydrolytic activity with a molecular mass close to 150 kDa, determined by comparison with the marker proteins.

D. Greater Than 75% of VIP Hydrolytic Activity Preserved In DEAE-Cellulose Chromatographed IgG After Ultrafiltration The IgG was diluted to 0.1 mg/ml and ultrafiltered on an Amicon YM-100 filter to 2.2 mg/ml. IgG precipitated with 50% saturated ammonium sulfate was centrifuged, redissolved in assay diluent, dialyzed and then assayed for hydrolytic activity as described in Example 5. Of the original VIP hydrolytic activity present in IgG purified by DEAE-cellulose chromatography, 78% and 80% was preserved in the retentate after ultrafiltration on a 100 kDa cutoff filter and in the ammonium sulfate precipitable fraction, respectively.

E. Treatment Of IgG With Anti-Human IgG And Removal Of Immunoprecipitate Decreased Hydrolytic Activity By 75%

Goat anti-human IgG (Antibodies Inc.) was purified further by chromatography on immobilized protein G as above. The human IgG (450 μg; 100 μl) was incubated with 700 μl of the anti-human IgG (diluted 13.5-fold) or assay diluent for 45 min at 4° C., the precipitate removed by centrifugation and the supernatants tested for VIP hydrolytic activity. Treatment of the IgG preparation with anti-human IgG and removal of the immunoprecipitate decreased the hydrolytic activity by 75%. The retention of a small proportion (25%) of the starting VIP hydrolytic activity in the supernatant was likely due to incomplete IgG precipitation.

EXAMPLE 9

Induction Of Catalytic Activity In Anti-VIP-Autoantibody
A. Ultrafiltration

IgG was prepared by chromatography on (i) protein G conjugated to Sepharose or (ii) DEAE-cellulose. The IgG (4 mg/ml) was ultrafiltered on a YM-10 membrane having an average cut off molecular weight of 10,000 Daltons using an Amicon Model 8 MC apparatus to 27 mg/ml, diluted back to 0.8 mg/ml and then subjected to a second cycle of ultrafiltration. The final concentration of IgG prepared in this manner was 20 mg/ml. IgG purified as above but without ultrafiltration and IgG purified with ultrafiltration as above were each incubated with mono(($^{125}$I-Tyr$^{10}$)-VIP in radioimmunoassay buffer at 4° C. for two hours in the presence of increasing unlabeled VIP concentrations and the TCA soluble radioactivity was determined as described in Example 7.

Figure 12:
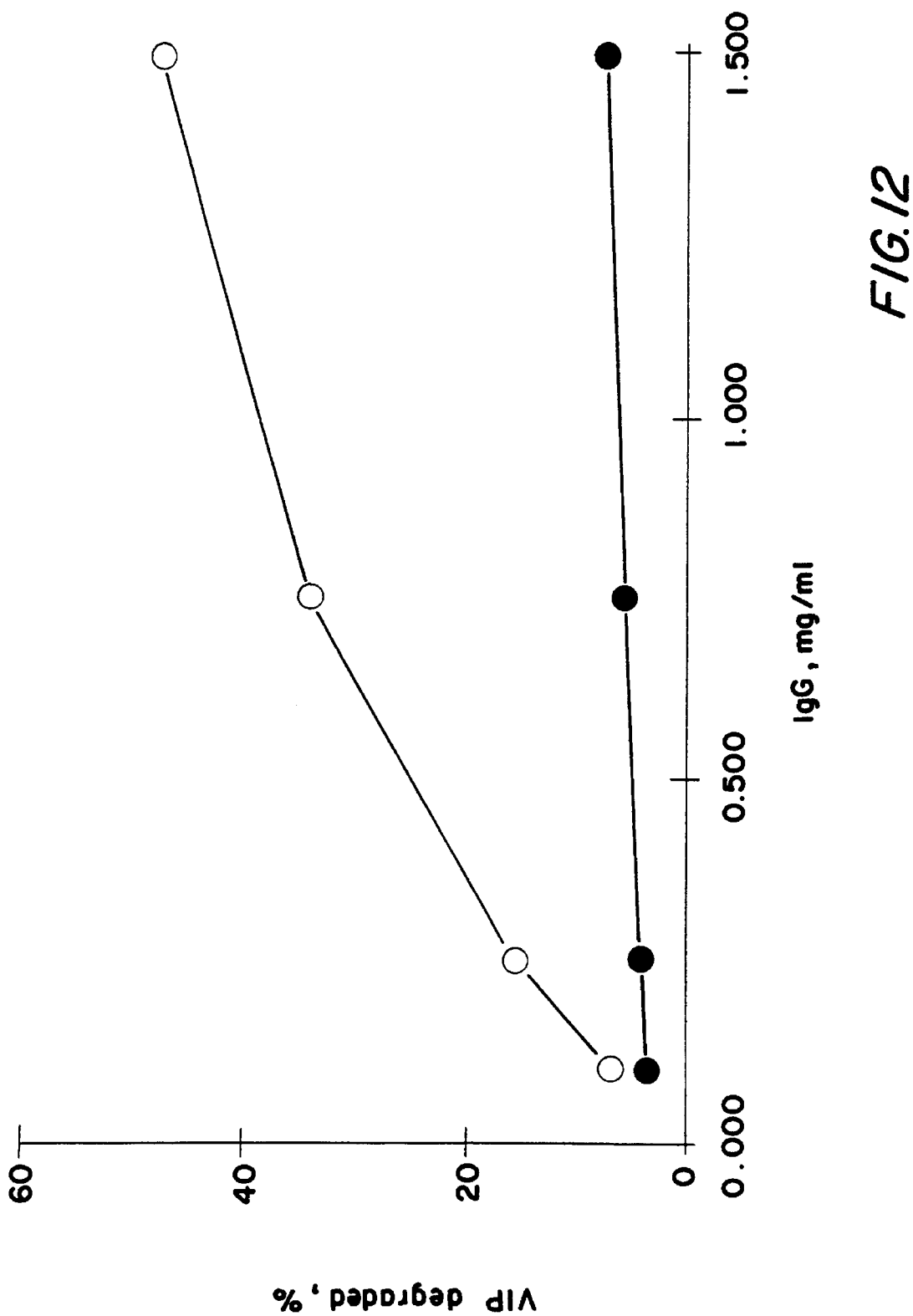
FIG. 12 is a plot of % VIP degraded versus concentration of IgG which (i) received no ultrafiltration (●) and (ii) received ultrafiltration (○).

FIG. 12 indicates that treatment of mono($^{125}$I, Tyr$^{10}$)-VIP with IgG that had not been subjected to ultrafiltration resulted in a dose-dependent, but low-level degradation of the peptide, judged by the increase in TCA-soluble radioactivity over the value obtained with assay buffer. IgG subjected to ultrafiltration degraded VIP better than IgG which had not been ultrafiltered.

B. Dialysis

IgG (2mg/ml), prepared by chromatography as described in A above, was dialyzed using a dialysis membrane with a cut-off of 12,000–15,000 Daltons for four days against 1000 volumes of buffer (50 mM Tris-HCl, 100 mM glycine, pH 8.0, containing 0.025% Tween-20), with daily buffer changes (a total of three changes). As with ultrafiltration, IgG subjected to dialysis degraded VIP better than IgG which had not been subjected to dialysis.

C. Washing After Immobilization On Protein-G

IgG (1 mg in 0.5 ml of buffer (50 mM Tris-HCl, 100 mM glycine, pH 8.0, containing 0.025% Tween-20), prepared by chromatography as described in A above, was applied to a Protein G-Sepharose column (settled volume, 3.3 ml) in order to immobilize the IgG on the Protein G. The immobilized IgG was then washed with 135 ml of neutral pH buffer (50 mM Tris-HCl, pH 7.3) followed by elution with a low pH buffer (100 mM glycine-HCl, pH 2.7). The acidic eluent was then neutralized immediately and the IgG isolated. As with ultrafiltration, IgG subjected to neutral buffer washes degraded VIP better than IgG which had not been subjected to such treatment.

D. Affinity Chromatography On VIP-Sepharose

IgG fractions containing VIP hydrolytic autoantibodies exhibit relatively tight binding of VIP. This property was used to purify specific catalytic VIP hydrolytic autoantibodies on a VIP-Sepharose column. IgG was purified from the plasma of a human subject by ammonium sulfate precipitation and DEAE-cellulose chromatography (8). The IgG was free of detectable non-immunoglobulin materials (27). To prepare the affinity chromatography matrix, synthetic VIP (1-28) (10 mg) mixed with about 20 pg ($Tyr^{10}$-$^{125}$I)-VIP was covalently coupled to 5g CNBr-Sepharose (5g; Pharmacia) in 0.1M $NaHCO_3$, pH7, in 0.5M NaCl for two hours at 4° C., and unreacted groups on the gel were quenched with 0.2M glycine in coupling buffer (26). The coupling efficiency was greater than 90%, based on incorporation of ($Tyr^{10}$-$^{125}$I)-VIP. About 90 mg IgG was shaken with 4.5 ml Of VIP-Sepharose gel at 4° C. and 0.5M Tris-HCL, pH 8.0 for 2 h. The mixture was poured into a column, the gel washed with buffer until the effluent $A_{280}$ (sensitivity 0.05 AUFS) returned to baseline, and bound IgG was eluted with 0.1M glycine-HCl, pH 2.7 and neutralized immediately with 1M Tris-HCl, pH 9.0. Antibody concentrations were estimated by scans ($A_{562}$) of silver-stained, non-reducing SDS-gels, using authentic IgG as standard (Gilford Response II spectrophotometer). Increasing authentic IgG concentrations (2-20 ng per lane) showed a linear increase in $A_{562}$ values. As with ultrafiltration, IgG subjected to affinity chromatography degraded VIP better than IgG which had not been subjected to affinity chromatography.

EXAMPLE 10

VIP Hydrolytic Activity of Supernatant From EBV Transformed Lymphocyte

Peripheral blood lymphocytes of an individual positive for hydrolytic VIP antibodies were transformed with Epstein-Barr virus by established procedures (14–19). The culture supernatants from these cells appeared to cause 53% hydrolysis of mono($^{125}$I-$Tyr^{10}$)-VIP, judged by the TCA precipitation method. Control fluid (RPMI with 10% fetal bovine serum) did not appear to cause significant hydrolysis and the culture supernatant of an irrelevant EBV transformed cell line appeared to cause 21% hydrolysis. A low level of saturable VIP binding activity (about CPM/100µl) was detected in the supernatant from EBV transformed cells of the VIP antibody positive subject, but not from the irrelevant cell line.

EXAMPLE 11

Preparation Of Human Hybridoma Cell Lines Producing Catalytic Anti-VIP Antibodies Lymphocytes are isolated by density gradient centrifugation on Ficoll-Hypaque. VIP-specific B lymphocytes are enriched by attachment to Petri dishes containing immobilized producing cell line) for 2 hours, washed and then cultured at $1\times10^6$/ml in RPMI-1640 supplemented with 10% fetal bovine serum, L-glutamine and antibiotics. The cultures of transformed cells are examined daily and fed twice weekly. After about two weeks immunoglobulins from the culture supernatants are examined for VIP binding and hydrolytic activity by the methods described above. The resulting EBV cell lines are cloned in 96 well cell culture plates by limiting dilution using 0.5 cells/well with 10% ORIGEN cloning factor (IGEN) in place of feeder layers. Positive growing clones are assayed for immunoglobulin production and screened for VIP hydrolytic activity. The cells producing the hydrolytic antibodies are recloned to ensure their monoclonal status. The positive cell cultures are expanded for immunoglobulin production and for hybridization with human or mouse myeloma cell lines. Since EBV transformed cell lines are often low immunoglobulin producers, transformed cells are hybridized with either mouse myelomas or a mouse-human heteromyeloma in order to obtain stable hybrids which produce the unique catalytic antibodies. Three different partners are used including the mouse myeloma: SP2/OAg14, the human plasmacytoma: SKO-007 and a mouse x human heteromyeloma: SHM-D33 grown in the presence of the antibiotic G-418 to stabilize the human chromosomes. The fusion is done in the same way as mouse x mouse fusions (20).

EXAMPLE 12

Characterization and Catalytic Activity of IgG Purified By Affinity Chromatography (Fractionation) on VIP-Sepharose A. VIP Hydrolysis ($Tyr^{10}$-$^{125}$I)-VIP (about 30 pH) mixed with increasing VIP concentrations was treated with the IgG or antibodies purified by affinity chromatography on VIP-Sepharose as in Example 8D for 3 h at 38° C. in 200 µl 0.05 M Tris-HCl, 0.1M glycine, pH 8, containing 0.025% Tween-20 and 0.1% BSA. The IgG and antibodies tested hydrolysis assays were previously dialyzed against 500 volumes of buffer for 4 days, with daily buffer changes. Hydrolysis of VIP was computed by measuring the radioactivity rendered soluble in TCA, corrected for the radioactivity observed after incubation in assay diluent (27). Catalysis by the antibody was determined in the absence and presence of VIP[22-28]. Data were fitted to the Michaelis-Menten equation by means of the ENZFITTER program (Elsevier). Reverse phase HPLC of antibody treated reaction mixtures was on a C18 column (27).

B. ($Tyr^{10}$-$^{125}$I) VIP Binding

IgG prepared by DEAE-cellulose chromatography was assayed for saturable ($Tyr^{10}$-$^{125}$I)-VIP binding (8), in the absence and presence of increasing concentrations of unlabeled VIP. Apparent $K_D$ for VIP was determined using EBDA and LIGAND programs (Elsevier) assuming (i) the binding had reached equilibrium, and (ii) the $K_D$ of ($Tyr^{10}$-$^{125}$I)-VIP and unlabeled VIP were identical.

C. Sodium Dodecylsulfate-Polyacrylamide Gel Electrophoresis (SDS-PAGE) and Isoelectric Focusing (IEF)

Electrophoresis of antibody preparations treated with 20 mM M 2-mercaptoethanol and 2.5% SDS (100° C., 5 min) was on Phast SDS-gradient gels (8–25%) (Pharmacia). The gel was stained with silver (28). For immunostaining, proteins were transferred to nitrocellulose (BAS5, Schleicher and Schuell) by diffusion blotting (30 min), the membrane was treated with blocking buffer (0.02M Tris-HCl, pH 7.4, 0.5M NaCl, 3% BSA, 0.05% Tween-20), then with rabbit anti-human H-chain (IgG) (1:1000) or anti-human L-chain (1:2,500) (Accurate) for 60 min, washed with buffer, treated with peroxidase conjugated goat anti-rabbit IgG (1:1000; Accurate), washed again and finally incubated with 0.5 mg diaminobenzidine/ml (Sigma) and 0.03% hydrogen peroxide for 10–30 min. IEF was on Phast IEF gels using a pH gradient of 3–10 constructed with Pharmalytes.

Figure 14:
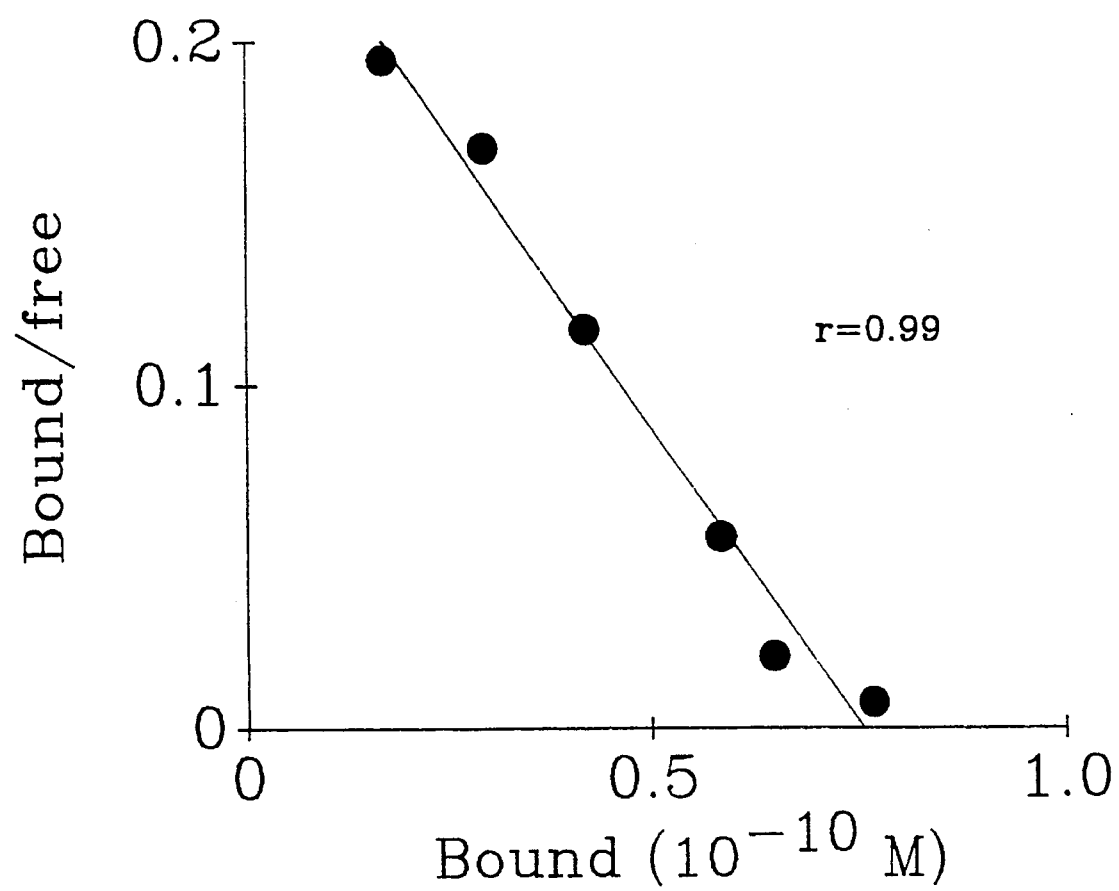
FIG. 14 is a Scatchard plot of VIP binding by the IgG.
Figure 15:
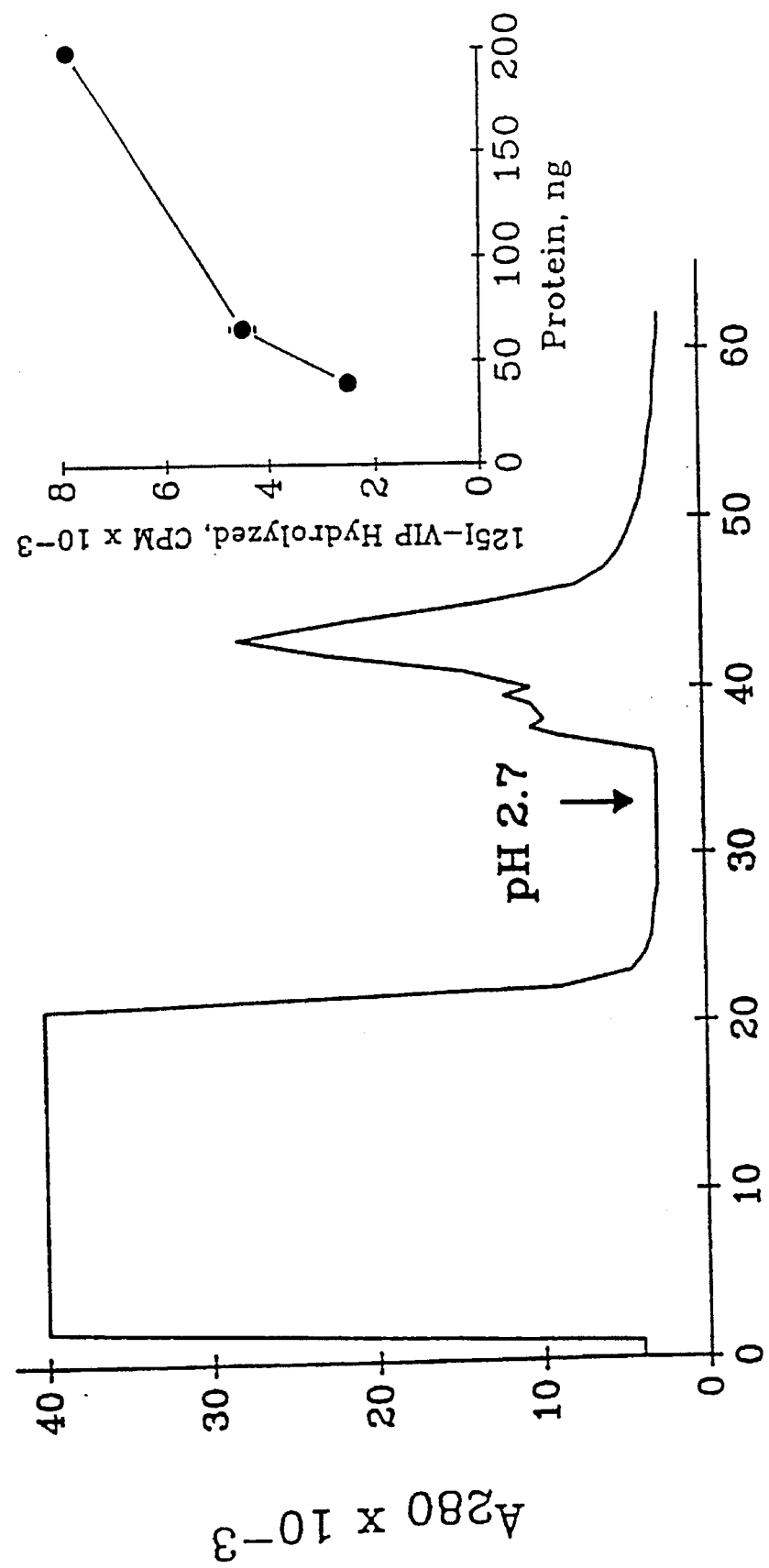
FIG. 15 shows an affinity chromatograph of human IgG on a VIP-Sepharose column, with the arrow indicating the shift to a low pH buffer and the inset shows hydrolysis of (Tyr$^{10}$-$^{125}$I) VIP as a function of concentration of acid eluted antibody concentration.
Figure 16:
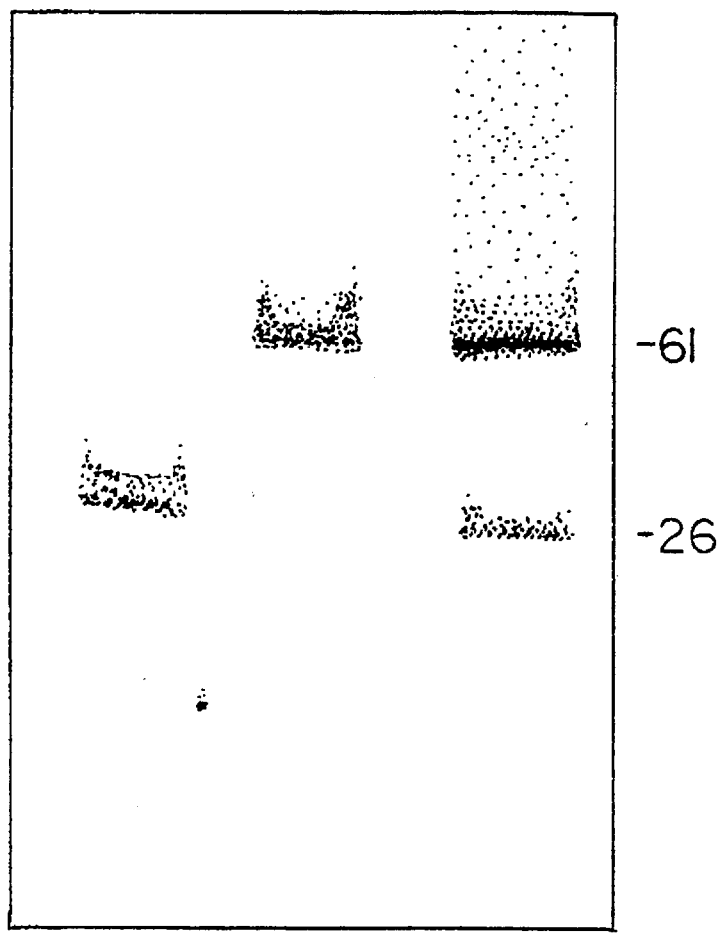
FIG. 16 shows reducing SDS-polyacrylamide gel electrophoresis of affinity-fractionated VIP autoantibodies stained with anti L-chain antibody (lane 1), anti-H-chain antibody (lane 2) and silver (lane 3).

D. Characterization of Anti-VIP Catalytic Autoantibody (Tyr$^{10}$-$^{125}$I)-IgG to VIP binding was measured using IgG that did not exhibit measurable VIP hydrolytic activity (i.e., IgG which had not been subjected to ultrafiltration, dialysis, Protein-G chromatography or affinity chromatography on VIP-Sepharose) judged by the amount of radioactivity precipitated in 10% TCA after incubation in assay diluent or immune IgG (87.9% and 91.0%). A Scatchard plot of VIP binding by the IgG revealed a single binding component (r=0.99) with $K_d$ 0.3 nM and VIP antibody concentration 184 fmol/mg IgG (FIG. 14; values shown in FIG. 14 are means of three replicates each). Progressively increasing (Tyr$^{10}$-$^{125}$I)VIP hydrolysis by increasing concentrations of the affinity-purified antibodies was observed, judged by the amount of radioactivity rendered soluble in TCA (FIG. 15). SDS-PAGE under reducing conditions indicated that the affinity-fractionated material was composed of 61 kD H-chains and 26 kD L-chains, judged by silver staining and reactivity with anti-H and anti-L chain antibodies in immunoblots (FIG. 16). The IEF profile of the affinity-fractionated preparation (pH range 3.0-10.5) revealed a restricted range of antibody species (approximately 12 closely spaced bands focused at pH 6.9–8.4), compared to unfractionated IgG (innumerable bands focused mainly at pH 7.1–9.5).

E. Hydrolytic Specificity And Catalysis By VIP Antibodies

Figure 17:
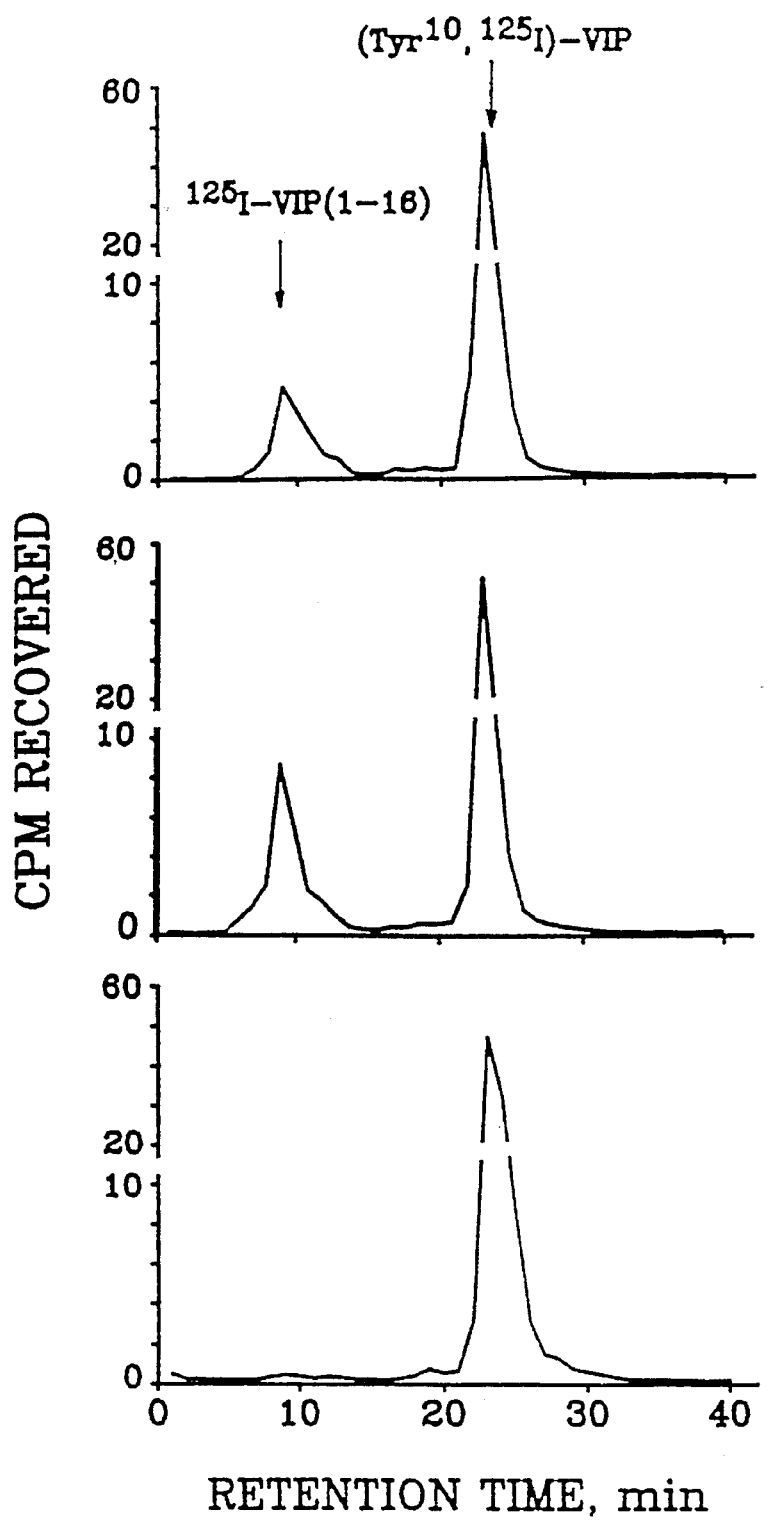
FIG. 17 shows reverse phase HPLC of (Tyr$^{10}$-$^{125}$I) VIP treated with unfractionated IgG (upper panel), affinity-fractionated VIP antibodies (middle panel), and assay diluent (lower panel), with arrows showing the retention time of synthetic ($^{125}$I)(VIP[1-16]) and unhydrolyzed (Tyr$^{10}$-$^{125}$I) VIP.
Figure 18:
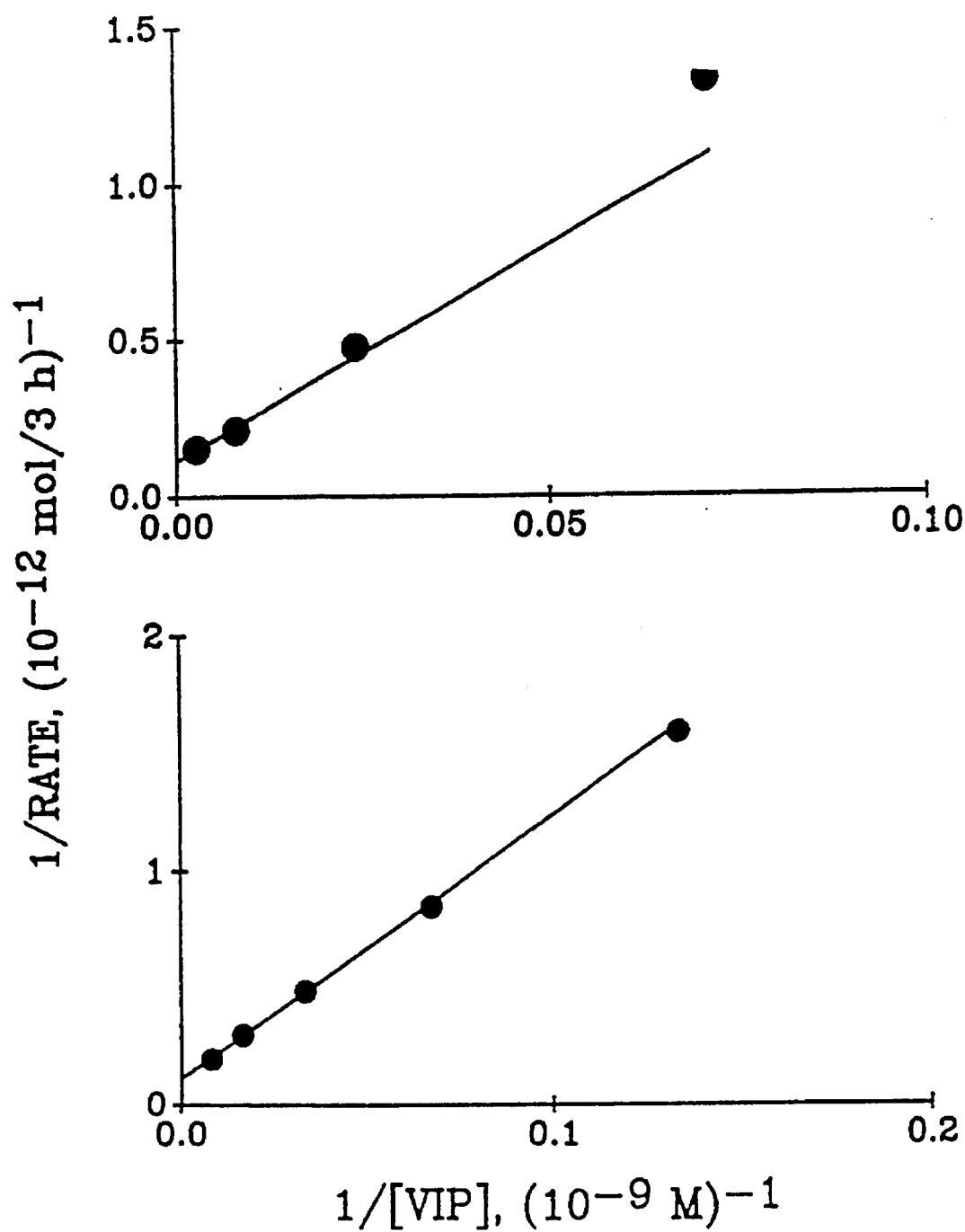
FIG. 18 shows Lineweaver-Burke plots of VIP hydrolysis by affinity-fractionated VIP antibodies (upper panel) and unfractionated IgG (lower panel).

The IgG preparation used here hydrolyzed the Gln$^{16}$-Met$^{17}$ bond in VIP (29). Thus, when (Tyr$^{10}$-$^{125}$I)VIP is used as substrate, one radioactive fragment, (Tyr$^{10}$-$^{125}$I)VIP(1-16), is generated. To compare their hydrolytic specificities, 100µg of unfractionated IgG and 0.3 µg of affinity-purified antibody were incubated with 210 pg (Tyr$^{10}$-$^{125}$I)VIP, and the reaction product characterized by reverse phase HPLC (FIG. 17). Treatment with both types of antibody preparations generated a single radioactive peptide with retention time identical to that of synthetic $^{125}$I-VIP[1-16] (8.2 min). This radioactive peptide was well resolved from unhydrolyzed (Tyr$^{10}$-$^{125}$I)VIP (retention time 21.5 min). These data suggested the peptide generated by the affinity-fractionated antibody and IgG is (Tyr$^{10}$-$^{125}$I)VIP[1-16] and therefore it was concluded that the affinity-purified antibody, like the unfractionated IgG, cleaved the Gln$^{16}$-Met$^{17}$ bond. Direct evidence that the antibody is a catalyst was obtained from the saturation kinetics of VIP hydrolysis. The affinity-fractionated antibody preparation was incubated with increasing VIP concentrations and a fixed (Tyr$^{10}$-$^{125}$I)VIP concentration (30 pM), and the radioactivity rendered soluble in TCA was measured. Plots of the reciprocal velocity versus reciprocal VIP concentration for affinity fractionated antibodies (66 ng) and for unfractionated IgG (300 µg) were essentially linear, suggesting conformity with Michaelis-Menton kinetics (FIG. 18). The $K_m$ value for the affinity-fractionated antibody was 110±3 nM, compared to 112±6 nM for unfractionated IgG. The turnover number of the antibody ($k_{cat}$), computed on the basis of the amount of total protein in the assay, was 0.11±0.01 min$^{-1}$. Comparison of the specific activities ($V_{max}$/ng total protein) of the affinity-fractionated antibody preparation and unfractionated IgG indicated a 2076-fold purification factor.

F. Kinetic Study

Study of the saturation kinetics displayed by the affinity-purified preparation provided direct evidence that the VIP-antibody is a catalyst. The antibody appeared to bind VIP relatively tightly ($K_m$ 110 nM), compared to conventional peptidases (30) and anti-hapten catalytic antibodies which exhibit $K_m$ values usually in the micromolar to millimolar range (31). The apparent high affinity substrate binding property of the VIP antibody is a desirable feature, since it is likely to confer stringent substrate specificity. Given that peptide bond hydrolysis is an energetically demanding chemical reaction, the calculated values of VIP antibody turnover number ($k_{cat}$ 0.11 min$^{-1}$) and kinetic efficiency ($k_{cat}/K_m$ 1.1×10$^6$ M$^{-1}$ min$^{-1}$) are impressive Although the IEF profile of the affinity-fractionated VIP antibodies revealed a restricted range of antibodies, it remains possible that the preparation may not be a homogeneous one. Thus, the $k_{cat}$ measured for the affinity-fractionated antibody preparation (0.11 min$^{-1}$) is a minimal value. The theoretical $k_{cat}$ value of the VIP antibody present in unfractionated IgG ($V_{max}$/amount of antibody, estimated from as the x-intercept of the Scatchard plot) was 6.5 min$^{-1}$. In comparison, the $k_{cat}$ and $k_{cat}/K_m$ values reported for an amidase antibody raised against a presumed transition state analog are 0.08 min$^{-1}$ and 1.4×10$^2$ M$^{-1}$min$^{-1}$, respectively (32). An antibody capable of Gly-Phe bond cleavage with metal co-factor assistance is purported to be a true catalyst with $k_{cat}$ 0.04 min$^{-1}$ but its saturation kinetics are not described (33).

EXAMPLE 13

Cleavage of VIP Peptide Bonds by Catalytic Antibody from Subject #5960 and subject #80

A. Iodinated Peptides

Human VIP(1-28) (Bachem) was labeled with $^{125}$I and Tyr$^{10}$-$^{125}$I)VIP was purified by reverse phase HPLC and identified by amino acid sequencing (27) The fragment VIP(15-28) was prepared by solid phase synthesis (University of Florida Core Facility, Gainesville) and its identity confirmed by amino acid analysis. Reverse phase HPLC on a C-18 column revealed a single $A_{214}$ absorbing peptide in this preparation. Iodination and purification of ($^{125}$I)VIP(15-28) was by the method used for preparation of (Tyr$^{10}$-$^{125}$I)VIP, except that a gradient of 16 to 40% acetonitrile in 0.1% trifluoroacetic acid (60 min) was used in the HPLC step. The ($^{125}$I)VIP(15-28) was recovered in the major radioactive peak with retention time 41.4 min. This peptide was subjected to 15 cycles of Edman's degradation using an Applied Biosystems 477A sequenator with online PTH-amino acid detection. The bulk of the radioactivity was recovered in cycle 8, and the radioactivity was observed to coelute with the PTH derivative of authentic mono$^{127}$I-tyrosine (Calbiochem). Thus, the VIP(15-28) was labeled with $^{125}$I at Tyr$^{22}$(Tyr$^{22}$-$^{125}$I)VIP(15-28).

B. Preparation of Antibodies

Autoantibodies to VIP were identified in the plasma of two human subjects (#5960 and #80) by measurement of saturable (Tyr$^{10}$-$^{125}$I)-VIP binding (4). IgG was purified from plasma by ammonium sulfate precipitation and protein G-Sepharose chromatography (27, 4). Fab was prepared by treatment of IgG with immobilized papain and protein A-agarose chromatography (27). Rabbit anti-human IgG (Accurate) was purified by protein-G Sepharose chromatography prior to its use in immunoprecipitation studies. Antibody concentrations were estimated by scans (A$_{562}$) of silver-stained non-reducing SDS-gels (see below), using authentic IgG as standard (Gilford Response II spectrophotometer). Increasing IgG concentrations (2–20 ng per lane) showed a linear increase in A$_{562}$ values.

C. Affinity Chromatography

To prepare the affinity chromatography matrix, 10 mg synthetic VIP(1-28) mixed with about 20 pg (Tyr$^{10}$-$^{125}$I) VIP was coupled covalently to CNBr-Sepharose (5 g; Pharmacia) in 0.1M NaHCO$_3$, pH 7, in 0.5M NaCl for 2 h at 4 C, and unreacted groups on the gel were quenched with 0.2M glycine in coupling buffer (as described in Example 9, part D above). The coupling efficiency was >90%, judged by incorporation of (Tyr$^{10}$-$^{125}$I)VIP. About 90 mg IgG was shaken with 4.5 ml VIP-Sepharose at 4° C. in 0.05M Tris-HCl, pH 8, for 2 h, the gel poured into a column, washed until the effluent A$_{280}$ (sensitivity 0.05 AUFS) had returned to the baseline value, bound antibody eluted with 0.1M glycine-HCl, pH 2.7, and neutralized immediately with 1M Tris-HCl, pH 9.

D. VIP Hydrolysis

A fixed concentration of (Tyr$^{10}$-$^{125}$I)-VIP (about 30 pM) mixed with increasing VIP concentrations was treated with the IgG, Fab or affinity-purified antibodies for 3 h at 38° C. in 200 µl 10.05M Tris-HCl, 0.1M glycine, pH 8, containing 0.025% Tween-20 and 0.1% BSA. The IgG and affinity-purified antibodies tested for hydrolytic activity were previously dialyzed against 500-volumes of buffer for 4 days, with daily buffer changes. Hydrolysis of VIP was computed by measuring the radioactivity rendered soluble in TCA, corrected for the radioactivity observed after incubation in assay diluent (27). Data were fitted to the Michaelis-Menten equation by means of the ENZFITTER program (Elsevier). The pH optimum, determined by varying the pH from 4 to 11 by addition of HCl or NaOH, was 8.0–8.5 for the hydrolytic IgG preparations from both human subjects.

E. Identification of Fragments of VIP

VIP (50 µg) was treated with IgG (588 µg; subject #5960) or antibodies purified by affinity chromatography on VIP-Sepharose (88 µg; subject #80), except that BSA was absent in the reaction mixture. Control incubations consisted of VIP incubated in assay diluent without IgG, VIP incubated with nonimmune IgG and IgG incubated without VIP. The reaction mixtures were extracted on C18 cartridges (Extract-Clean, Alltech) and analyzed by reverse phase HPLC on a Novapak C18 column using gradients of acetonitrile in TFA as described (27). Peptide peaks observed in the antibody-treated VIP preparations, and absent in control reaction mixtures, were sequenced with a pulsed liquid phase sequenator with online PTH-amino detection (Applied Biosystems, model 477A). When (Tyr$^{22}$, $^{125}$I)VIP(15-28) was employed as substrate, the reaction products were purified by reverse phase HPLC as before, and the presence of radioactivity in each of 15 amino acid sequencing cycles was determined.

F. Identification of the Scissile Bonds Cleaved by Antibody of Subject #5960 and #80

The VIP antibody fractions were purified from the blood of the human subjects (#5960 and #80) by affinity chromatography on immobilized protein G and VIP-Sepharose. Increasing amounts of IgG (0.5-100 µg) from both individuals caused progressively increasing hydrolysis of (Tyr$^{10}$-$^{125}$I)VIP (3–40%), judged by the amount of radioactivity rendered soluble in trichloroacetic acid (27). The pH optima for antibodies were 8.0 and 8.5 (not shown). Reverse phase HPLC profiles indicated that multiple radioactive fragments of VIP with retention times distinct from that of intact (Tyr$^{10}$-$^{125}$I)VIP (34.6 min) were present in the reaction mixtures. This suggested multiple cleavage sites in VIP, since the radioactive peptide was labeled with $^{125}$I at a single residue (Tyr$^{10}$). To identify the scissile bonds, unlabeled VIP was treated with the antibodies purified by chromatography on VIP-Sepharose (subject #80) or protein G-Sepharose (subject #5960), and the peptide fragments were separated and sequenced. In control incubations, VIP was treated with nonimmune IgG or assay diluent. Nine peptide fractions (FIG. 13A) produced by treatment with antibodies from subject #80 were absent in control incubations. In each case, the deduced sequence of the peptides present in the nine fractions was found to align with subsequences found in full-length VIP. The scissile bonds were identified based on detection of peptide fragments that: (i) contained an N-terminal residue other than the N-terminal His of full-length VIP, (ii) had an amino acid sequence at least 5 residues in length identical to an internal subsequence of VIP, and (iii) sequenced at the level of 10 pmoles or more. Five VIP fragments satisfying the criteria defined above were generated by antibodies from subject #80. The peptide bonds in VIP located on the N-terminal side of these fragments were identified as the scissile bonds (Table 1). Several fractions contained N-terminal fragments of full-length VIP. Due to progressively decreasing yields of the PTH-amino acids in successive sequencing cycles, the C-terminal residues of these peptides could not be assigned with certainty, with one exception. This exception was a peptide present in fraction 3, which was identified as VIP(1-14) because it sequenced at >100 pmole per residue up to its C-terminal Arg. On the basis of these data, it has been determined that the antibodies from subject #80 cleave VIP at six bonds. Similar methods were employed to identify the bonds cleaved by antibodies (IgG) from the second subject (subject #5960). Numerous peptide peaks noted after treatment of VIP with these antibodies were absent in control incubations (FIG. 13B). Two peptide pools were constructed, consisting of fractions with retention times 1.5 min–10.5 min. and 11.5–22.5 min. These pools were rechromatographed using gradients of acetonitrile in TFA (12–40% and 16–48%, respectively). Ten peptide peaks were sequenced. Seven fragments were identified that met with the criteria defined for localization of the scissile bonds (Table 2). These data show that seven of the nine peptide bonds in the region spanning residues 14 to 22 can be cleaved by antibodies, and one is found at residues 7–8.

TABLE 1

| Peptide Bonds Cleaved by Antibodies from Subject 80 | |
|---|---|
| Fraction #* Cleavage Site | N-Terminal Sequence** |
| 2 Lys$^{21}$—Tyr$^{22}$ | Y—L—N—S—I |
|  | K—Y—L—N—S |
| Lys$^{20}$—Lys$^{21}$ |  |
| 3 Ala$^{18}$—Val$^{19}$ | V—K—K—Y—L |
| 4 Met$^{17}$—Ala$^{18}$ | A—V—K—K—Y |
| 9 Gln$^{16}$—Met$^{17}$ | M—A—V—K—K |

Figure 13A:
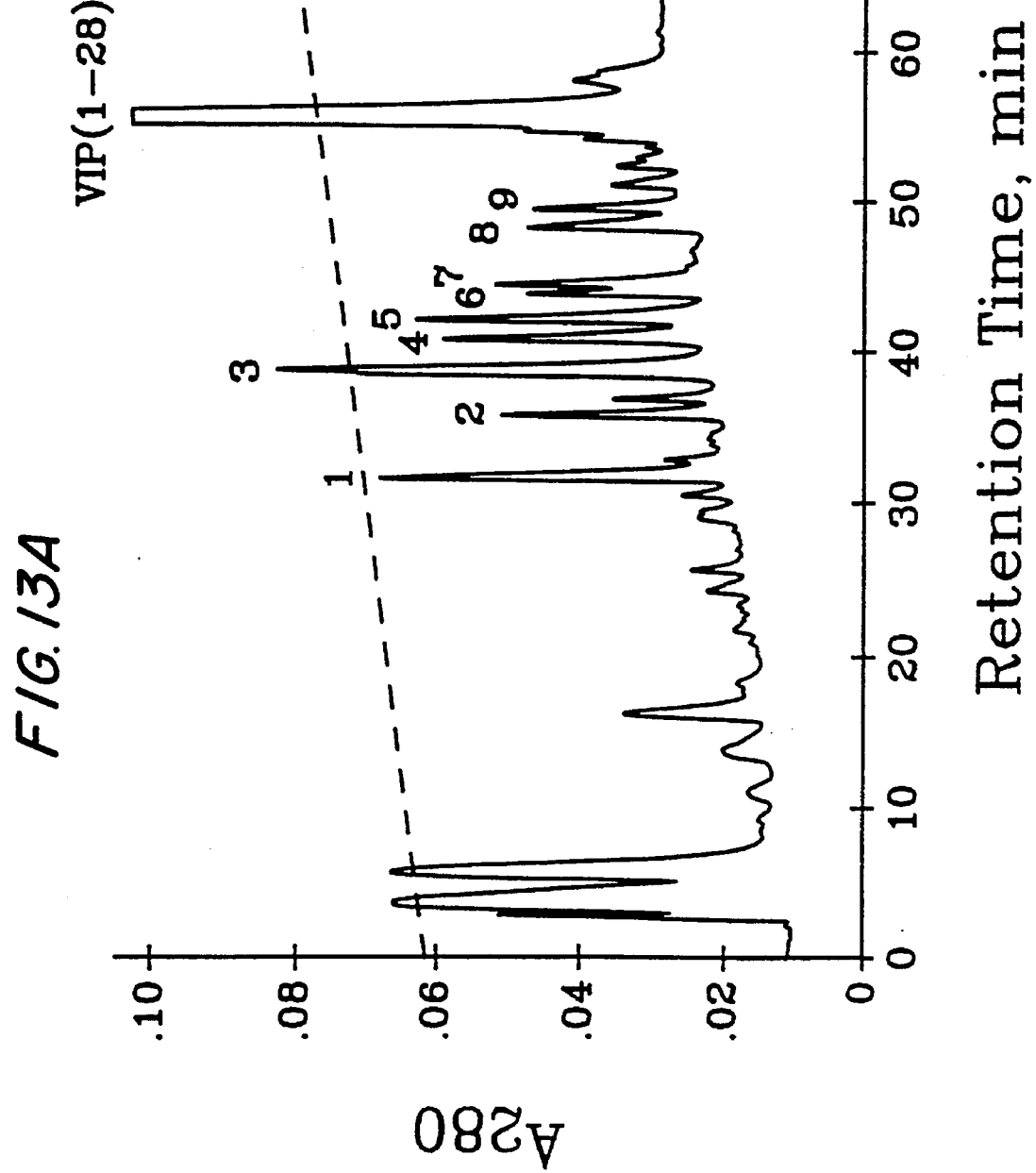
FIG. 13(A) Reverse phase HPLC separation of peptides produced by treatment of VIP with antibodies from subject #80. Peaks 1–9 were sequenced.
Figure 13B:
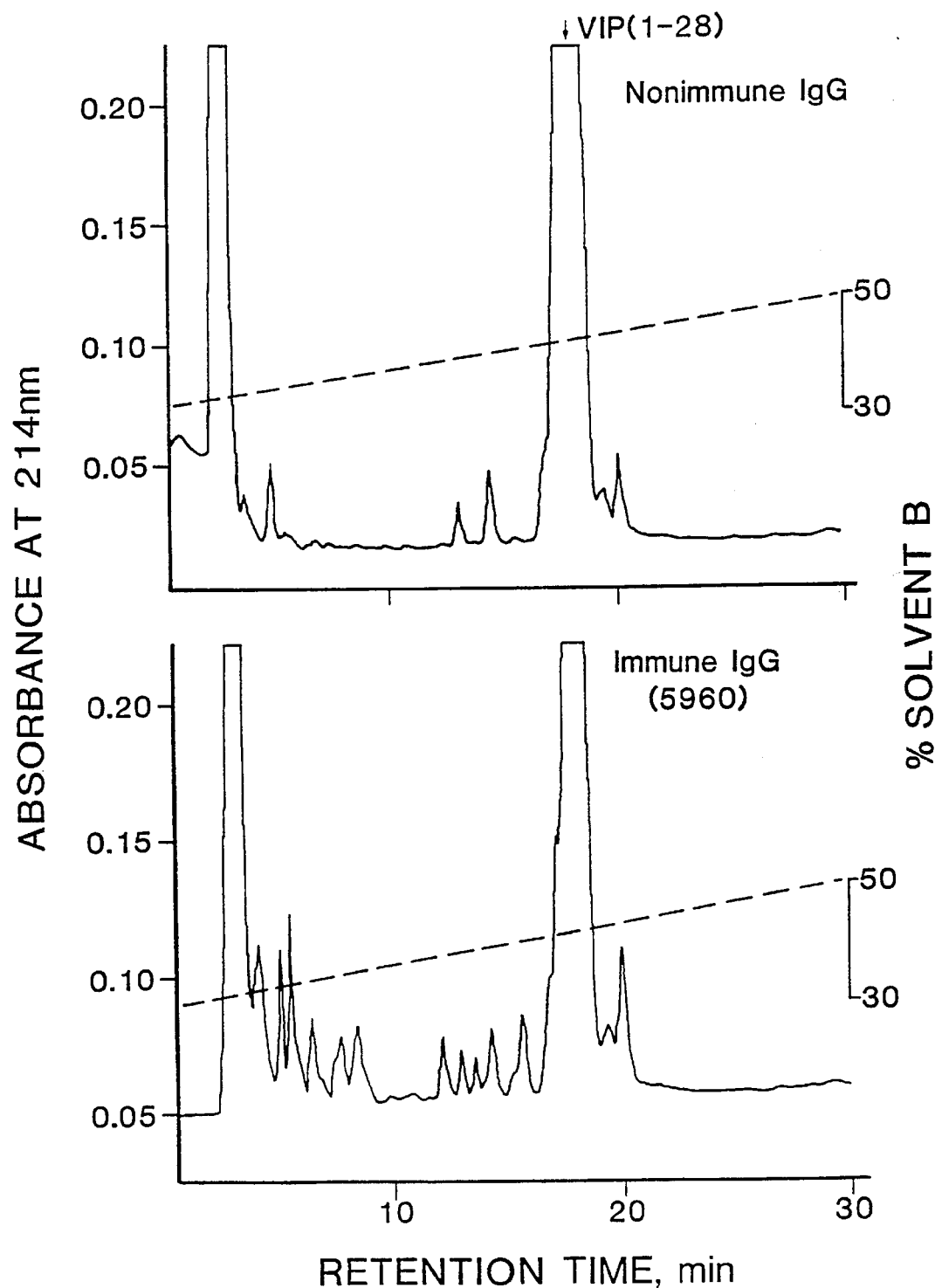
FIG. 13(B) Reverse phase HPLC profiles of VIP after treatment with antibodies (IgG) from subject #5980 (lower panel) and non-immune IgG (upper panel).
Figure 13C:
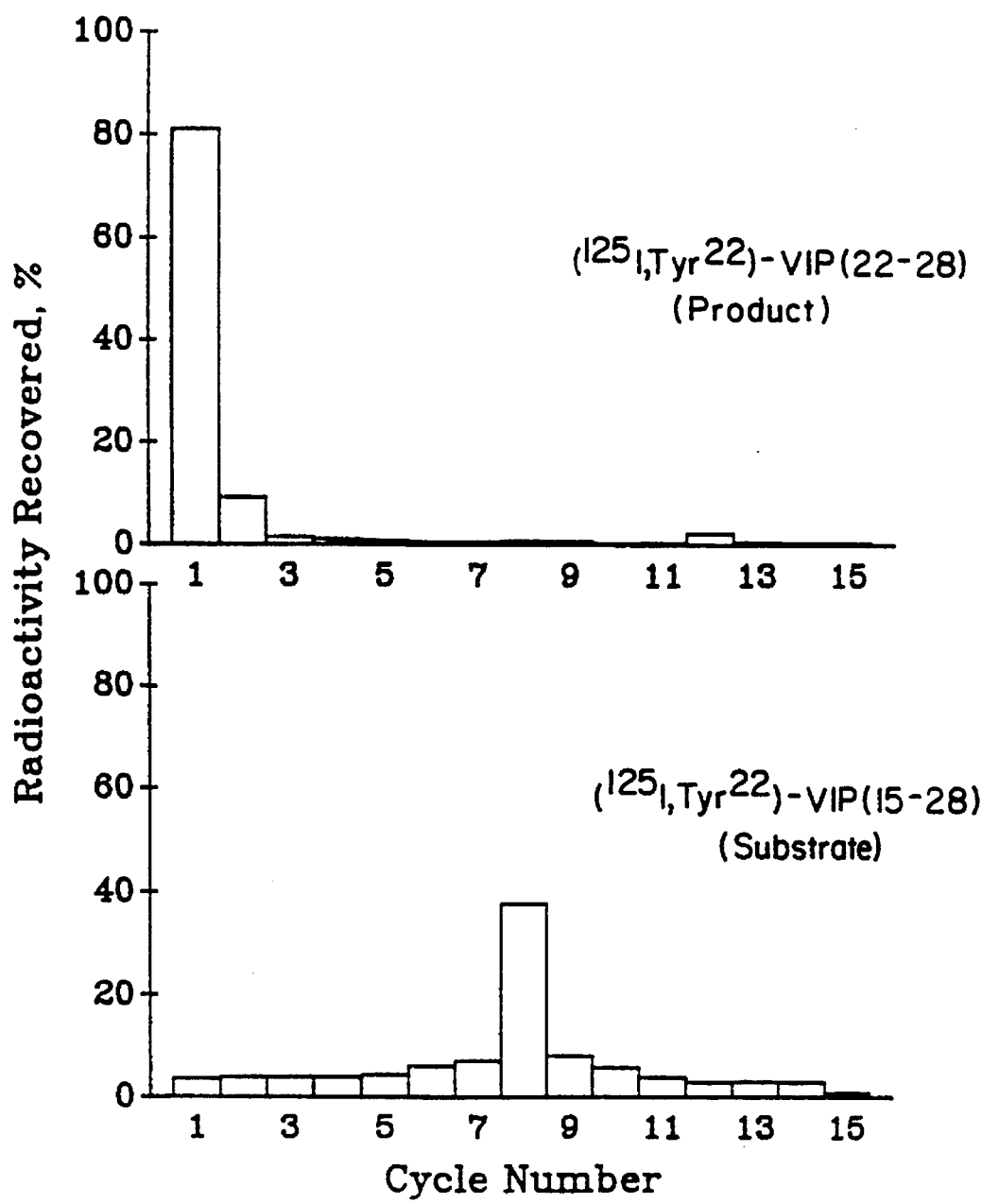
FIG. 13 (C) Radiosequencing of intact (Tyr$^{22}$-$^{125}$I)VIP(15-28) (lower panel) and its cleavage product, (Tyr$^{22}$-$^{125}$I)VIP(22-28), recovered after treatment of (Tyr$^{22}$-$^{125}$I)VIP(15-28) with antibodies (IgG) from subject #5960 and separation by reverse phase HPLC. The retention times of (Tyr$^{22}$-$^{125}$I)VIP(15-28) and (Tyr$^{22}$-$^{125}$I)VIP(22-28) peaks were 37.5 min and 43 min.

*Obtained from FIG. 13A fractions 1, 5, 6, 7 and 8 did not contain VIP fragments that met the criteria defined in the text.
**Data are for the first 5 sequencing cycles.

TABLE 2

Peptide Bonds Cleaved by Antibodies from Subject #5960

| Fraction #*<br>Cleavage Site | N-Terminal Sequence** |
|---|---|
| 3 | K—Y—L—N—S |
| $Lys^{20}$—$Lys^{21}$ | |
| | Y—L—N—S—I |
| $Lys^{21}$—$Tyr^{22}$ | |
| 4 | V—K—K—Y—L |
| $Ala^{18}$—$Val^{19}$ | |
| 6 | A—V—K—K—Y |
| $Met^{17}$—$Ala^{18}$ | |
| 8 | M—A—V—K—K |
| $Gln^{16}Met^{17}$ | |
| 9 | M—A—V—K—K |
| $Gln^{16}$—$Met^{17}$ | |
| | K—Q—M—A—V |
| $Arg^{14}$—$Lys^{15}$ | |
| 10 | D—N—Y—T—R |
| $Thr^{7}$—$Asp^{8}$ | |

*Obtained by two rounds of reverse phase HPLC, the first of which is depicted in FIG. 13B fractions 1, 2, 5 and 7 did not contain VIP fragments that met the criteria defined in the text.
**Data are for the first 5 sequencing cycles.

REFERENCES

1. Pauling, L. *Nature* 161:707, 1948.
2. Kohen, F., Kim., J. B., Lindner, H. R., Eshhar, Z., Green, B. Antibody enhanced hydrolysis of steroid esters FEBS.
3. S. J. Pollack, J. W. Jacobs, P. G. Schultz, *Science* 234, 1570 (1986); A. Tramontano, A. A. Amman, R. A. Lerner, *J. Am. Chem Soc.* 110, 2282 (1988); K. D. Janda, D. Schloeder, S. J. Benkovic, R. A. Lerner, *Science* 241, 1188 (1988); C. N. Durfor, R. J. Bolin, R. J. Sugasawara, R. J. Massey, J. W. Jacobs, P. G. Schultz, *J. Am. Chem. Soc.* 110, 8713 (1988).
4. D. Y. Jackson, J. W. Jacobs, R. Sugasawara, S. H. Reich, P. A. Bartlett, P. G. Schultz, *J. Am. Chem. Soc.* 110, 4841 (1988); D. Hilvert, S. H. Carpenter, K. D. Nared, N. T. Auditor, *Proc., Natl. Acad. Sci. USA* 85, 4953 (1988).
5. K. Shokat, C. H. Leumann, R. Sugasawara, P. G. Schultz, *Angew. Chem. Int. Ed. Engl.* 27, 1172 (1988).
6. Paul, S., H. Erian, P., Said, S. I. Autoantibody to vasoactive intestinal peptide in human circulation. *Biochem. Biophys. Res. Commun,* 130:479–485, 1985.
7. Paul, S., Said, S. I. Human autoantibody to vasoactive intestinal peptide: Increased incidence in muscular exercise. *Life Sciences* 43:1079–1084, 1988.
8. Paul, S., Said, S. I., Thompson, A., Volle, D. J., Agrawal, D. K., Foda, H., De la Rocha, S.: Characterization of autoantibodies to VIP in asthma. *J. Neuroimmunol.* 23:133–142, 1989.
9. Itoh, N., Obata, K.-I., Yanaihara N., Okamoto, H. Human preprovasoactive intestinal polypeptide contains a novel PHI-27-like peptide, PHM-27, *Nature* 304:547–549, 1983.
10. Bloom, S. R., Barnes, A. J., Adrian, T. E., Polak, J. M. Autoimmunity in diabetics induced by hormonal contaminants of insulin. *Lancet* i:14–17, 1979.
11. Paul, S., Said, S. I. Characterization of receptors for vasoactive intestinal peptide from the lung. *J. Biol. Chem.* 262:158–162, 1987.
12. Paul, S., Wood, K., Said, S. I. Purification of [($^{125}$I]-Vasoactive intestinal peptide by reverse-phase HPLC. *Peptides* 5:1085–1087, 1984.
13. Turner, J. T., Bylund, D. B. Characterization of the VIP receptor in rat submandibular gland: Radioligand binding assay in membrane preparations *J. Pharmacol Exp. Therap.* 242:873–881, 1987.
14. Steinitz, M., Klein, G., Koskimies, S., Makela, 0., EB Virus induced B lymphocyte lines producing specific antibodies. *Nature* 269:420–422, 1977.
15. Steinitz, M., Seppala, I., Eichmann, K., Klein, G. Establishment of a Human Lymphoblastoid Cell Line with Specific antibody production against group A streptococcal carbohydrate. *Immunobiology* 156:41–47, 1979.
16. Steinitz, M., Izak, G., Cohen, S., Ehrenfeld, M., Flechner, I. Continuous production of monoclonal rheumatoid Factor by EBV-transformed lymphocytes. *Nature* 287:443–445, 1980.
17. Kozbor, D., Steinitz, M., Klein, G., Koskimies, S., Maketa, O. Establishment of anti-TNP antibody-producing human lymphoid lines by preselection for hapten binding followed by EBV transformation. *Scand. J. Immunol.* 1.10:187–194, 1979.
18. Kozbor, D. & Roder, J. The production of monoclonal antibodies from human lymphocytes. *Immunology Today* 4:72–79, 1983.
19. Roder, J., Cole, D., Kozbor, D. The EBV-Hybridoma Technique, *Methods in Enzymology* 121:140–167, 1986.
20. Kohler G., Milstein C. Continuous Cultures of Fused Cells Secreting Antibody of Predefined Specificity. *Nature* 256:445–497 (1975)
21. Sacerdote, P. et al., *J. of Neuroscience Res.*, 18, 102–107 (1987);
22. Dimaline, R. et al., *Biochemica et Biophysica Acta.* 930, 97–100 (1987).
23. Opstad, K., *Peptidases,* 8, 175–178 (1986);
24. Unkeless, J. C. et al., *Ann. Rev. Immunol.* 6, 251–81 (1988);
25. Hendershot, L. M. et al., *Mol. and Cellular. Bio.*, 8 (10), 4250–5256 (1988); and
26. *Affinity Chromatography Principles and Methods*, Pharmacia, Uppsala Sweden pp. 12–18 (1986).
27. Paul, S., Volle, D. J., Beach, C. M., Johnson, D. R. Powell, M. J. and Massey, J. J. *Science,* 244: 1158–1162 (1989).
28. *PhastGel Silver Kit Instruction Manual.* Pharmacia (Uppsala, Sweden 1987).
29. Baldwin, E. and Schultz, P. G., Generation of a catalytic antibody by site-directed mutagenesis. *Science.* 244:1152 (1989).
30. Dixon, M., Webb, E. C. et al., Enzymes, 3d Ed. Longman, (London 1979); Fisher, G. Acyl group transfer-Aspartic proteinases. *Enzyme Mechanisms*, M. I. Page and A. Williams, eds., Royal Society of Chemistry, 230 (London 1987).
31. Janda, K. D. et al., supra ref. 3; Schultz, P. G. Catalytic antibodies. *Acc. Chem. Res.* 22:287 (1989); Blackburn, G. M., Kang, A. S. et al. Catalytic antibodies. *Biochem. J.* 262:381 (1989).
32. Janda, K. D. et al., supra ref. 3.
33. Iversen, B. L. and Lerner, R. A., *Science* 243:1184 (1989).

What is claimed is:

1. An extract of blood serum comprising an autoantibody which catalytically enhances the rate of cleavage of a peptide bond in a substrate, said extract having been prepared by a process comprising the steps of:

(a) identifying an animal with autoantibodies to a self-antigen of said animal;

(b) isolating an extract of blood serum containing said autoantibodies; and (c) screening said extract containing said autoantibodies to identify an autoantibody which catalytically enhances the rate of said cleavage:

wherein said substrate is selected from the group consisting of a peptide hormone, a peptide neurotransmitter, a peptide neuromodulator, a viral protein, a bacterial protein, and a tumor protein.

2. An extract as recited in claim 1, wherein said substrate is a self-antigen of said animal.

3. An extract as recited in claim 1, wherein said peptide hormone is insulin.

4. A method for preparing an autoantibody which catalytically enhances the rate of cleavage of a peptide bond in a substrate, comprising the steps of:
   (a) identifying an animal with autoantibodies to a self-antigen of said animal;
   (b) isolating said autoantibodies; and
   (c) screening said autoantibodies to identify an autoantibody which catalytically enhances the rate of said cleavage;
   wherein said substrate i selected from the group consisting of a peptide hormone, a peptide neurotransmitter, a peptide neuromodulator, a viral protein, a bacterial protein, and a tumor protein.

5. A method as recited in claim 4, further comprising the steps of:
   (a) separating the gamma globulin fraction from serum of said animal;
   (b) separating from said gamma globulin fraction molecule(s) which bind to said gamma globulin fractions.

6. A method as recited in claim 5, wherein said molecule(s) which bind to said gamma globulin are separated from said gamma globulin by ultrafiltration.

7. A method as recited in claim 5, wherein said molecule(s) which bind to said gamma globulin are separated from said gamma globulin by dialysis.

8. A method as recited in claim 5, wherein said molecule(s) which bind to said gamma globulin are separated by chromatography on protein G-Sepharose.

9. A method as recited in claim 5, wherein said molecule(s) is separated from said gamma globulin by affinity chromatography on VIP Sepharose.

10. A method as recited in claim 4 wherein said autoantibody is a monoclonal antibody, further comprising the steps of:
    (a) isolating lymphocytes from said identified animal;
    (b) producing a plurality of hybridomas from said lymphocytes; and
    (c) screening the monoclonal antibodies produced by said hybridomas to identify monoclonal antibodies which catalytically enhance the rate of said cleavage.

11. A method as recited in claim 4 further comprising the steps of:
    (a) isolating lymphocytes from said identified animal;
    (b) transforming said lymphocytes with a virus;
    (c) stimulating said lymphocytes to grow in culture; and
    (d) screening the antibodies produced by said transformed lymphocytes to identify antibodies which catalytically enhance the rate of said cleavage.

12. A method as recited in claim 11, wherein said lymphocytes are stimulated by transformation with Epstein Barr virus.

13. A method as recited in claim 4, wherein said substrate is said self-antigen of said animal.

14. A method as recited in claim 4, wherein said peptide hormone is insulin.

15. A composition comprising an amount, effective for catalytically enhancing the rate of cleavage of a peptide bond in a substrate, of:
    (a) an extract of blood serum comprising an autoantibody which catalytically enhances the rate of said cleavage, said autoantibody having been prepared by a process comprising the steps of:
        (i) identifying an animal with autoantibodies to a self-antigen of said animal;
        (ii) isolating said autoantibodies; and
        (iii) screening said autoantibodies to identify antibody which catalytically enhances the rate of said cleavage; and
    (b) an inert carrier;
    wherein said substrate is selected from the group consisting of a peptide hormone, a peptide neurotransmitter, a peptide neuromodulator, a viral protein, a bacterial protein, and a tumor protein.

16. An autoantibody which catalytically enhances the rate of cleavage of a peptide bond in a substrate, said autoantibody having been prepared by the process comprising the steps of:
    (a) identifying an animal with autoantibodies to a self-antigen of said animal;
    (b) isolating said autoantibodies; and
    (c) screening said autoantibodies to identify an autoantibody which catalytically enhances the rate of said cleavage;
    wherein said substrate is selected from the group consisting of a peptide hormone, a peptide neurotransmitter, a peptide neuromodulator, viral protein, a bacterial protein, and a tumor protein.

17. The autoantibody as recited in claim 16, wherein said substrate is said self-antigen.

18. An isolated antibody capable of catalytically enhancing the rate of cleavage of a peptide bond in a substrate.

19. An isolated autoantibody capable of catalytically enhancing the rate of cleavage of a peptide bond in a substrate.

20. An autoantibody as recited in claim 19, wherein said substrate is a self-antigen.

21. A method for preparing an autoantibody which catalytically enhances the rate of cleavage of a peptide bond in a substrate, comprising the steps of:
    (a) identifying an animal with autoantibodies to a self-antigen of said animal;
    (b) isolating said autoantibodies; and
    (c) ultrafiltering said autoantibodies to identify an autoantibody which catalytically enhances the rate of said cleavage;
    wherein said substrate is selected from the group consisting of a peptide hormone, a peptide neurotransmitter, a peptide neuromodulator, a viral protein, a bacteria protein, and a tumor protein.

22. A method as recited in claim 21, wherein said substrate is said self-antigen of said animal.

23. An autoantibody capable of catalytically enhancing the rate of cleavage of a peptide bond in a substrate, said autoantibody having been prepared by the process comprising the steps of:
    (a) identifying an animal with autoantibodies to a self-antigen of said animal;
    (b) isolating said autoantibodies; and
    (c) screening said autoantibodies to identify an autoantibody which catalytically enhances the rate of said cleavage.

24. An autoantibody as recited in claim 23, wherein said substrate is said self-antigen of said animal.

25. An extract as recited in claim 1, wherein said peptide bond is between amino acid residues 7 and 8 in vasoactive intestinal peptide.

26. An extract as recited in claim 1, wherein said peptide bond is between amino acid residues 14 and 15 in vasoactive intestinal peptide.

27. An extract as recited in claim 1, wherein said peptide bond is between amino acid residues 17 and 18 in vasoactive intestinal peptide.

28. An extract as recited in claim 1, wherein said peptide bond is between amino acid residues 18 and 19 in vasoactive intestinal peptide.

29. An extract as recited in claim 1, wherein said peptide bond is between amino acid residues 20 and 21 in vasoactive intestinal peptide.

30. An extract as recited in claim 1, wherein said peptide bond is between amino acid residues 21 and 22 in vasoactive intestinal peptide.

31. An autoantibody as recited in claim 19, wherein said peptide bond is between amino acid residues 7 and 8 in vasoactive intestinal peptide.

32. An autoantibody as recited in claim 19, wherein said peptide bond is between amino acid residues 14 and 15 in vasoactive intestinal peptide.

33. An autoantibody as recited in claim 19, wherein said peptide bond is between amino acid residues 17 and 18 in vasoactive intestinal peptide.

34. An autoantibody as recited in claim 19, wherein said peptide bond is between amino acid residues 18 and 19 in vasoactive intestinal peptide.

35. An autoantibody as recited in claim 19, wherein said peptide bond is between amino acid residues 20 and 21 in vasoactive intestinal peptide.

36. An autoantibody as recited in claim 19, wherein said peptide bond is between amino acid residues 21 and 22 in vasoactive intestinal peptide.

37. A method as recited in claim 4, wherein said peptide bond is between amino acid residues 7 and 8 in vasoactive intestinal peptide.

38. A method as recited an claim 4, wherein said peptide bond is between amino acid residues 14 and 15 in vasoactive intestinal peptide.

39. A method as recited an claim 4, wherein said peptide bond is between amino acid residues 17 and 18 in vasoactive intestinal peptide.

40. A method as recited an claim 4, wherein said peptide bond is between amino acid residues 18 and 19 in vasoactive intestinal peptide.

41. A method as recited an claim 4, wherein said peptide bond is between amino acid residues 20 and 21 in vasoactive intestinal peptide.

42. A method as recited an claim 4, wherein said peptide bond is between amino acid residues 21 and 22 in vasoactive intestinal peptide.

43. An isolated extract of blood serum comprising an antibody which catalytically enhances the rate of cleavage of a peptide bond in a substrate, said extract having been prepared by a process comprising the steps of:

(a) identifying an animal with antibodies to a self-antigen of said animal;

(b) isolating an extract of blood serum containing said antibodies; and (c) screening said extract containing said antibodies to identify an antibody which enhances the rate of said cleavage;

wherein said substrate is selected from the group consisting of a peptide hormone, a peptide neurotransmitter, a peptide neuromodulator, a vital protein, a bacterial protein, and a tumor protein.

44. An extract as recited in claim 43, wherein said substrate is a self-antigen of said animal.

45. An extract as recited in claim 43, wherein said peptide hormone is insulin.

46. An isolated extract of blood serum comprising an antibody which catalytically enhances the rate of cleavage of a peptide bond in vasoactive intestinal peptide.

\* \* \* \* \*